United States Patent
Gebert-Schwarzwaelder et al.

(10) Patent No.: US 10,413,498 B2
(45) Date of Patent: *Sep. 17, 2019

(54) AGENTS FOR DYEING KERATIN FIBERS, CONTAINING AT LEAST ONE DIMERIC, DICATIONIC AZO DYE AND AT LEAST ONE ANIONIC AND/OR CATIONIC SURFACTANT

(71) Applicant: Henkel AG & Co. KGaA, Duesseldorf (DE)

(72) Inventors: Antje Gebert-Schwarzwaelder, Neuss (DE); Helmut Giesa, Meerbusch (DE); Astrid Kroos, Monheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,530

(22) PCT Filed: Oct. 14, 2015

(86) PCT No.: PCT/EP2015/073775
§ 371 (c)(1),
(2) Date: May 22, 2017

(87) PCT Pub. No.: WO2016/083012
PCT Pub. Date: Jun. 2, 2016

(65) Prior Publication Data
US 2017/0266094 A1  Sep. 21, 2017

(30) Foreign Application Priority Data

Nov. 25, 2014  (DE) .................. 10 2014 223 935

(51) Int. Cl.
| | | |
|---|---|---|
| A61Q 5/10 | (2006.01) | |
| A61K 8/49 | (2006.01) | |
| A61K 8/39 | (2006.01) | |
| A61K 8/41 | (2006.01) | |
| A61Q 5/06 | (2006.01) | |
| C09B 31/14 | (2006.01) | |

(52) U.S. Cl.
CPC ............... *A61K 8/496* (2013.01); *A61K 8/39* (2013.01); *A61K 8/416* (2013.01); *A61K 8/4946* (2013.01); *A61Q 5/065* (2013.01); *C09B 31/14* (2013.01); *A61K 2800/4324* (2013.01)

(58) Field of Classification Search
CPC .......... A61K 8/496; A61K 8/39; A61K 8/416; A61Q 5/065; C09B 31/14
See application file for complete search history.

(56) References Cited

U.S. PATENT DOCUMENTS

| | | | |
|---|---|---|---|
| 4,562,249 A | 12/1985 | Schwander et al. | |
| 4,563,191 A | 1/1986 | Hahnke et al. | |
| 4,607,071 A | 8/1986 | Haehnke et al. | |
| 7,407,516 B2 | 8/2008 | Vidal | |
| 2001/0001333 A1 | 5/2001 | Samain | |
| 2004/0200009 A1* | 10/2004 | Vidal | C09B 44/126 8/405 |
| 2004/0244124 A1 | 12/2004 | Plos et al. | |
| 2005/0235433 A1 | 10/2005 | Rondeau | |
| 2006/0112502 A1* | 6/2006 | Cotteret | A61Q 5/10 8/405 |
| 2012/0325261 A1* | 12/2012 | Hashimoto | A61Q 5/10 132/208 |
| 2014/0101868 A1* | 4/2014 | Hoffmann | A61K 8/891 8/407 |
| 2014/0165301 A1 | 6/2014 | Schweinsberg et al. | |
| 2014/0289970 A1 | 10/2014 | Gross et al. | |

FOREIGN PATENT DOCUMENTS

| | | |
|---|---|---|
| CA | 2303209 A1 | 3/1999 |
| DE | 2822912 A1 | 11/1979 |
| DE | 4128490 A1 | 3/1993 |
| EP | 3531943 A1 | 3/1993 |
| EP | 1609456 A1 | 12/2005 |
| EP | 1483334 B1 | 7/2007 |
| EP | 1448156 B1 | 8/2007 |
| FR | 2915681 A1 | 11/2008 |
| GB | 910121 A | 11/1962 |
| GB | 1186753 A | 4/1970 |
| GB | 1189753 A | 4/1970 |
| WO | 02100369 A2 | 12/2002 |

OTHER PUBLICATIONS

STIC Search Report dated Aug. 1, 2017.*
EPO, International Search Report and Written Opinion issued in International Application No. PCT/EP2015/073775, dated Dec. 1, 2015.
EPO, International Search Report and Written Opinion issued in International Application PCT/EP2015/072773, dated Nov. 12, 2015.
Preliminary Amendment for U.S. Application entitled "Agents for Dyeing Keratin Fibers, Containing at Least One Dimeric, Dicationic Azo Dye and at Least One Anionic Surfactant".
Substitute Specification for U.S. Application entitled "Agents for Dyeing Keratin Fibers, Containing at Least One Dimeric, Dicationic Azo Dye and at Least One Anionic Surfactant".
EPO, International Search Report and Written Opinion issued in International Application PCT/EP2015/073779, dated Nov. 30, 2015.
Preliminary Amendment for U.S. Application entitled "Agents for Dyeing Keratin Fibres, Containing at Least One Dimeric, Dicationic Azo Dye With Special Substitution Pattern".

(Continued)

*Primary Examiner* — Eisa B Elhilo
(74) *Attorney, Agent, or Firm* — Lorenz & Kopf, LLP

(57) ABSTRACT

The present disclosure relates to agents for dyeing keratin fibers, in particular human hair, containing, in a cosmetic carrier (a) at least one direct dye of formula (I), wherein Y1, Y2 independently represent a nitrogen atom or a group C—R9, and Q represents a special linker group of formula (II), (III), (IV) or (V), (b) at least one anionic surfactant and/or at least one cationic surfactant.

20 Claims, No Drawings

(56) References Cited

OTHER PUBLICATIONS

Substitute Specification for U.S. Application entitled "Agents for Dyeing Keratin Fibres, Containing At Least One Dimeric, Dicationic Azo Dye With Special Substitution Pattern".
EPO, International Search Report and Written Opinion issued in International Application PCT/EP2015/072774, dated Nov. 23, 2015.
Preliminary Amendment for U.S. Application entitled "Agents for Dyeing Keratin Fibers, Containing At Least One Dimeric, Dicationic Azo Dye and At Least One Non-Ionic Surfactant".
Substitute Specification for U.S. Application entitled "Agents for Dyeing Keratin Fibers, Containing At Least One Dimeric, Dicationic Azo Dye and At Least One Non-Ionic Surfactant".
EPO, International Search Report and Written Opinion issued in International Application No. PCT/EP2015/073776, dated Nov. 30, 2015.
Preliminary Amendment for U.S. Application entitled "Agents for Dyeing Keratin Fibers, Containing At Least One Dimeric, Ring-Bridged Azo Dye".
Substitute Specification for U.S. Application entitled "Agents for Dyeing Keratin Fibers, Containing At Least One Dimeric, Ring-Bridged Azo Dye".
USPTO, Office Action in U.S. Appl. No. 15/528,529 dated Aug. 31, 2017.
USPTO, Office Action in U.S. Appl. No. 15/528,538 dated Aug. 30, 2017.
USPTO, Office Action in U.S. Appl. No. 15/528,539 dated Aug. 31, 2017.
USPTO, Office Action in U.S. Appl. No. 15/528,532 dated Aug. 31, 2017.
STIC Search Report dated Jul. 29, 2017 (U.S. Appl. No. 15/528,529).
STIC Search Report dated Jul. 2, 2017 (U.S. Appl. No. 15/528,538).
STIC Search Report dated Aug. 6, 2017 (U.S. Appl. No. 15/528,539).
STIC Search Report dated Jun. 28, 2017 (U.S. Appl. No. 15/528,532).

* cited by examiner

AGENTS FOR DYEING KERATIN FIBERS, CONTAINING AT LEAST ONE DIMERIC, DICATIONIC AZO DYE AND AT LEAST ONE ANIONIC AND/OR CATIONIC SURFACTANT

CROSS-REFERENCE TO RELATED APPLICATION

This application is a U.S. National-Stage entry under 35 U.S.C. § 371 based on International Application No. PCT/EP2015/073775, filed Oct. 14, 2015 which was published under PCT Article 21(2) and which claims priority to Application no. 10 2014 223 935.4, filed Nov. 25, 2014, which are all hereby incorporated in their entirety by reference.

TECHNICAL FIELD

The present disclosure pertains to agents for dyeing keratinous fibers, in particular, human hair, which contain (a) at least one dimeric dicationic azo dye of a specific formula (I) in combination with (b) at least one anionic and/or cationic surfactant. It has been found that the use of specific anionic surfactants (b) makes it possible to raise the color intensity of cationic azo dyes of formula (I). Another subject matter of the present disclosure is therefore the use of anionic surfactants (b) to improve the color take-up performance of cationic azo dyes of formula (I) onto keratinous fibers.

BACKGROUND

It has furthermore been found that the use of specific cationic surfactants (b) also makes it possible to raise the color intensity of cationic azo dyes of formula (I). Another subject matter of the present disclosure is therefore the use of specific cationic surfactants (b) to improve the color take-up performance of cationic azo dyes of formula (I) onto keratinous fibers.

As a general rule, either direct dyes or oxidation dyes may be used for dyeing keratinous fibers. Although intense colors with good fastness properties can be obtained with oxidation dyes, the development of the color generally takes place under the influence of oxidizing agents such as $H_2O_2$, for example, which in some cases may result in damage to the fiber. Furthermore, some oxidation dye precursors or certain mixtures of oxidation dye precursors may have a sensitizing effect on people with sensitive skin. Direct dyes are applied under gentler conditions. The disadvantage of these dyes, however, lies in the fact that the colors often have inadequate fastness properties.

A person skilled in the art uses direct dyes of different dye classes depending on the desired color result. The direct dyes known from the prior art include, for example, the classes of nitro dyes, anthraquinone dyes, azo dyes, triarylmethane dyes, or methine dyes. All of these dye classes should meet a specific requirement profile for use in the field of cosmetics. Thus, direct dyes should deliver an intense dyeing result and possess the best possible fastness properties. The color result obtained with direct dyes should be affected as little as possible by environmental influences, i.e., the dyes should have, for example, favorable wash fastness, light fastness, and friction fastness. The color result should also be altered as little as possible by chemical influences to which the keratinous fibers may be exposed after the dyeing process (e.g., permanent waves).

In order to bleach simultaneously with the dyeing, the direct dyes should also be as compatible as possible with the oxidizing agents (e.g., hydrogen peroxide and/or persulfates) commonly used in blonding processes.

For intense bleaching of dark hairs, hydrogen peroxide is not used alone, but rather a combination of hydrogen peroxide and persulfates (e.g., ammonium persulfate, potassium persulfate, and/or sodium persulfate). If, then, dark hair is to be bleached intensely in one step and simultaneously dyed in a bright shade, it is advantageous to use a mixture of hydrogen peroxide, persulfates, and a direct dye. Although many intensive-dyeing direct dyes would be known to a person skilled in the art in order to dye hair, a person skilled in the art only knows a very limited selection of dyes that exceed the strong oxidative conditions, such as represented by a mixture of the above-mentioned oxidizing agents, without decomposition. In addition, the oxidation-stable dyes that are known in the prior art have serious drawbacks with respect to the other fastness properties thereof.

There has thus been a need for dies that have high stability against strong oxidizing agents, in order to simultaneously dye and intensely bleach hair. These dyes should also not lose the positive fastness and dyeing properties thereof, even under these extreme usage conditions.

It has been shown that bright and intense coloration can be achieved, in particular, with cationic direct dyes. Cationic dyes are often distinguished by particularly elevated affinity for keratin fibers, a characteristic which may be attributed to the interactions of the positive charges of the dyes with negatively charged structural components of the keratinous fibers. Accordingly, it is often possible to achieve particularly intense colorings with cationic dyes.

Examples of well-known monomeric cationic azo dyes known from the prior art include the representatives Basic Orange 31 (alternative name: 2-[(4-Aminophenyl)azo]-1,3-dimethyl-1H-imidazolium chloride, CAS-Nr. 97404-02-9) and Basic Red 51 (alternative name: 2-[((4-Dimethylamino)phenyl)azo]-1,3-dimethyl-1H-imidazolium chloride, CAS-Nr. 77061-58-6).

Both dyes dye keratinous fibers with excellent color intensity in orange to red shades. There is still also a need for direct blue dyes that are optimally compatible with both of these dyes.

BRIEF SUMMARY

Agents for dyeing keratinous fibers are provided herein. In an exemplary embodiment, an agent for dyeing keratinic fibers includes, in a cosmetic carrier, (a) at least one direct dye of formula (I),

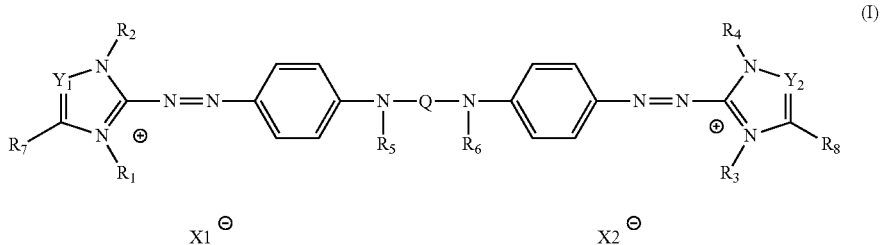

wherein

R1, R2, R3, R4 represent, independently of one another, a $C_1$-$C_6$ alkyl group, a $C_2$-$C_6$ alkenyl group, or a hydroxy $C_2$-$C_6$ alkyl group;

R5, R6 represent, independently of one another, a hydrogen atom, a $C_1$-$C_6$ alkyl group, a $C_2$-$C_6$ alkenyl group, a hydroxy $C_2$-$C_6$ alkyl group, or a cyano $C_1$-$C_6$ alkyl group;

R7, R8 represent, independently of one another, a hydrogen atom, a $C_1$-$C_6$ alkyl group, a halogen atom from the group consisting of chlorine, bromine, fluorine, and/or iodine, or a $C_1$-$C_6$ alkoxy group;

Y1, Y2 represent, independently of one another, a nitrogen atom or a group C—R9;

R9 represents a hydrogen atom, a $C_1$-$C_6$ alkyl group, a halogen atom from the group consisting of chlorine, bromine, fluorine, and/or iodine, or a $C_1$-$C_6$ alkoxy group;

X1, X2 represent, independently of one another, a physiologically acceptable anion, chloride, bromide, iodide, methyl sulfate, methyl sulfonate, p-toluenesulfonate, acetate, hydrogen sulfate, ½ sulfate, or ½ tetrachlorozincate;

Q represents a group of formula (II), (III), (IV), or (V);

*—($CH_2$)$n$—*     (II)

*—($CH_2$)$m$—O—($CH_2$)$p$—*     (III)

*—($CH_2$)$m$—O—($CH_2$)$p$—O—($CH_2$)$q$—*     (IV)

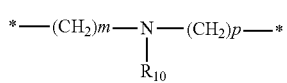     (V)

n represents an integer from 3 to 6;

m, p, q represent, each independently of one another, the number 2 or 3;

R10 represents a hydrogen atom, a $C_1$-$C_6$ alkyl group, a $C_2$-$C_6$ alkenyl group, or a hydroxy $C_2$-$C_6$ alkyl group;

and (b) at least one anionic surfactant and/or at least one cationic surfactant.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present application therefore addresses the problem of providing dyes for keratinous fibers, in particular, human hair, that have favorable technical properties in terms of the depth of color and the fastness properties, in particular, light, friction, and wash fastness, as well as perspiration and cold wave fastness. In case of simultaneous use with oxidation dyes and/or oxidizing agents, the direct dyes should have high stability against hydrogen peroxide and other oxidizing agents, and should maintain the positive fastness and dyeing properties. Additionally, the brightest and most intense colorations possible in the red range should be obtained.

Moreover, the aforementioned dyes should also be especially compatible with the cationic azo dyes Basic Orange 31 and Basic Red 51.

It has surprisingly been found that these problems can be largely solved if dyes of the following formula (I) are used in combination with at least one anionic surfactant and/or cationic surfactant in the agents for dyeing keratinous fibers.

A first subject matter of the present disclosure is an agent for oxidatively dyeing keratinous fibers, in particular human hair, containing—in a cosmetic carrier— a. at least one direct dye of formula (I)

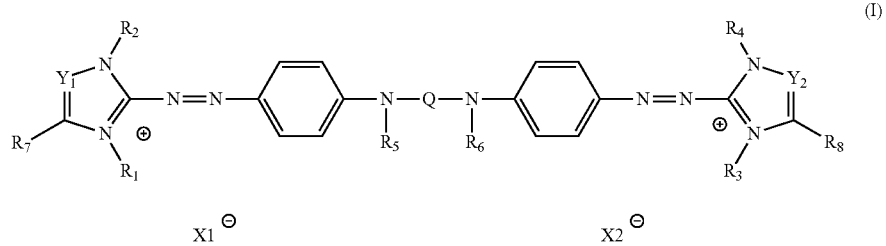

wherein
R1, R2, R3, R4 represent—independently of one another—a $C_1$-$C_6$ alkyl group, a $C_2$-$C_6$ alkenyl group, or a hydroxy $C_2$-$C_6$ alkyl group;
R5, R6 represent—independently of one another—a hydrogen atom, a $C_1$-$C_6$ alkyl group, a $C_2$-$C_6$ alkenyl group, a hydroxy $C_2$-$C_6$ alkyl group, or a cyano $C_1$-$C_6$ alkyl group;
R7, R8 represent—independently of one another—a hydrogen atom, a $C_1$-$C_6$ alkyl group, a halogen atom from the group consisting of chlorine, bromine, fluorine, or iodine, or a $C_1$-$C_6$ alkoxy group;
Y1, Y2, represent—independently of one another—a nitrogen atom or a group C—R9;
R9 represents a hydrogen atom, a $C_1$-$C_6$ alkyl group, a halogen atom from the group consisting of chlorine, bromine, fluorine, or iodine, or a $C_1$-$C_6$ alkoxy group;
X1, X2 represent—independently of one another—a physiologically acceptable anion, preferably from the group consisting of chloride, bromide, iodide, methyl sulfate, methyl sulfonate, p-toluenesulfonate, acetate, hydrogen sulfate, ½ sulfate, or ½ tetrachlorozincate;
Q represents a group of formula (II), (III), (IV), or (V);

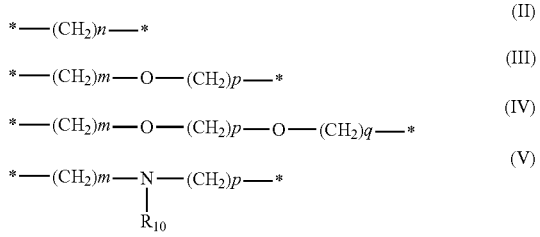

n represents an integer from 3 to 6;
m, p, q represent—each independently of one another—the number 2 or 3;
R10 represent a hydrogen atom, a $C_1$-$C_6$ alkyl group, a $C_2$-$C_6$ alkenyl group, or a hydroxy $C_2$-$C_6$ alkyl group;
and
b. at least one anionic surfactant and/or at least one cationic surfactant.

Keratinous fibers, keratin-containing fibers, or keratin fibers are understood to mean fur, wool, feathers, and in particular human hair. Although the agents according to the present disclosure are primarily suited for bleaching keratin fibers, use in other fields is also possible in principle.

The term "dyeing keratin fibers" used according to the present disclosure includes any form of changing the color of fibers. It includes, in particular, the color changes covered by the terms tinting, blonding, matting, oxidative dyeing, semipermanent dyeing, permanent dyeing and temporary dyeing. It explicitly also includes color changes according to the present disclosure presenting a lighter color result in comparison to the original color, such as for example coloring blonding processes. The term "matting (of) keratin fibers" is understood to mean the counteracting of undesired shifts in shade that occur when the color of keratin fibers is changed oxidatively, especially with blonding or bleaching processes. The purpose of matting is to attenuate the orange to reddish color impression brought about by incomplete blonding, and produce a silvery-cool color perception after the blonding process. The active ingredients that are used with matting may be applied in the form of a post-treatment step after the blonding or bleaching of the keratin fibers. It is, however, also possible for the active ingredients used for the matting to be applied to the keratin fibers together with the blonding agent or bleaching agent, within the framework of a one-step method. Suitable active ingredients that can be used for the matting include direct dyes—whether alone or in the dye mixture—that have the suitable color properties. It is moreover possible to use direct dyes in combination with oxidation dye precursors (developers and couplers) for the matting.

The agents according to the present disclosure contain the direct dyes of formula (I) in a cosmetic carrier. This cosmetic carrier is preferably aqueous, alcoholic, or aqueous-alcoholic. For purposes of the hair treatment, such carriers may be, for example, creams, emulsions, gels, or also surfactant-containing foaming solutions such as shampoos, foam aerosols, or other preparations that are suitable for application to the hair. It would, however, also be possible to prepare a formulation in the form of a powder or even in the form of tablets, for storage. This is then blended before use in an aqueous solvent or with organic solvents or with mixtures of water and organic solvents to obtain the application mix. An aqueous carrier contains, within the meaning of the present disclosure, at least 40% by weight, in particular, at least 50% by weight water. Within the meaning of the present disclosure, aqueous-alcoholic carriers are understood to be water-containing compositions containing 3 to 70% by weight a $C_1$-$C_4$ alcohol, in particular, ethanol or isopropanol. The agents according to the present disclosure may additionally contain further organic solvents, for example, 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred. Preferred agents according to the present disclosure are wherein additionally containing a non-aqueous solvent, wherein preferred agents according to the present disclosure contain the solvent at a concentration of about 0.1 to 30% by weight, preferably at a concentration of about 1 to 20% by weight, especially preferably at a concentration of about 2 to 10% by weight, in each case relative to the agent.

As a first essential ingredient (a), the agents according to the present disclosure contain at least one dye of formula (I).

The substituents R1 to R10 of the compounds of formula (I) are explained by way of example below: Examples of a $C_1$-$C_6$ alkyl group are the methyl, ethyl, propyl, isopropyl, n-butyl, s-butyl, and t-butyl, n-pentyl, and n-hexyl groups. Propyl, ethyl, and methyl are preferred alkyl residues. Examples of a $C_2$-$C_6$ alkenyl group are vinyl, allyl, but-2-enyl, but-3-enyl, and isobutenyl, preferred $C_2$-$C_6$ alkenyl residues being vinyl and allyl. Preferred examples of a hydroxy $C_1$-$C_6$ alkyl group are a hydroxymethyl, 2-hydroxyethyl, 2-hydroxypropyl, 3-hydroxypropyl, 4-hydroxybutyl, 5-hydroxypentyl, and 6-hydroxyhexyl group, a 2-hydroxyethyl group being particularly preferred. Preferred examples of cyano $C_1$-$C_6$ alkyl groups are the cyanomethyl group, 2-cyanoethyl group, and 3-cyanopropyl group. Halo $C_1$-$C_6$ alkyl groups which are preferred according to the present disclosure are the chloromethyl group, the bromomethyl group, the fluoromethyl group, the 2-chloroethyl group, the 2-bromoethyl group, the 2-fluoromethyl group, the 2-chloropropyl group, the 2-bromopropyl group, the 2-fluoropropyl group, the 3-chloropropyl group, the 3-bromopropyl group and the 3-fluoropropyl group. Halogen atoms are selected from the group consisting of chlorine, bromine, fluorine, and/or iodine, where chlorine and bromine are especially preferred. Notable examples of a $C_1$-$C_6$ alkoxy group include the methoxy, ethoxy, and propoxy groups.

The compounds of general formula (I) bear the residues R1, R2, R3, and R4; herein, the residues R1 to R4 may be the same or different. Preferably, R1 to R4 represent—independently of one another—a $C_1$-$C_6$ alkyl group or a $C_2$-$C_6$ alkenyl group. Especially preferably, the residues R1 to R4 represent—independently of one another—a $C_1$-$C_6$ alkyl group, in particular, a methyl group or an ethyl group.

In an especially preferred embodiment, an agent according to the present disclosure is wherein containing (a) at least one direct dye of general formula (I), in which
R1, R2, R3, R4 represent—independently of one another—a methyl group or an ethyl group.

The compounds of general formula (I) also bear the residues R5, and R6; herein, the residues R5 to R6 may be the same or different. Preferably, R5 and R6 represent—independently of one another—a hydrogen atom, a $C_1$-$C_6$ alkyl group, or a $C_2$-$C_6$ alkenyl group.

R7 and R8 represent—independently of one another—a hydrogen atom, a methyl group, or a methoxy group. Very especially preferably, R7 and R8 both represent a hydrogen atom.

In another especially preferred embodiment, an agent according to the present disclosure is wherein containing (a) at least one direct dye of general formula (I), in which R7, R8 represent—independently of one another—a hydrogen atom, a methyl group, or a methoxy group, preferably a hydrogen atom.

In the direct dyes of formula (I), the residues Y1 and Y2 are each a component of the two cationic heterocyclic ring systems contained in the formula. In a dye of formula (I), Y1 and Y2 may be the same or different; preferably, Y1 and Y2 are the same. Y1 and Y2 represent—independently of one another—a nitrogen atom or a group C—R9.

If both representing a nitrogen atom, then Y1 and Y2 entail compounds of formula (Ia):

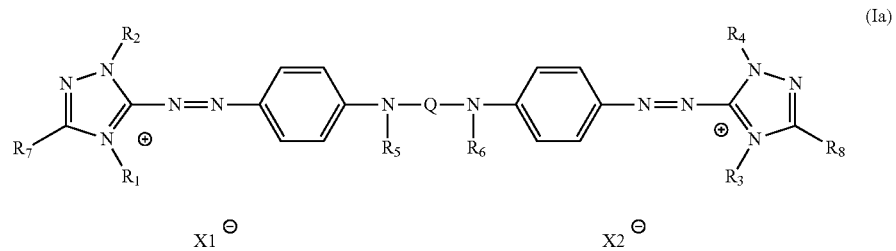

(Ia)

Especially preferably, R5 and R6 represent—independently of one another—a hydrogen atom or a $C_1$-$C_6$ alkyl If both representing C—R9 group, then Y1 and Y2 entail compounds of formula (Ib).

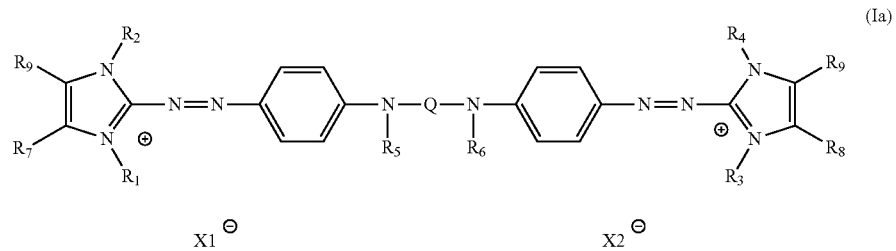

(Ia)

group. Very especially preferably, R5 and R6 represent—independently of one another—a hydrogen atom, a methyl group, or an ethyl group.

In an especially preferred embodiment, an agent according to the present disclosure is wherein containing (a) at least one direct dye of general formula (I), in which
R5, R6 represent—independently of one another—a hydrogen atom, a methyl group, or an ethyl group.

In a very especially preferred embodiment, an agent according to the present disclosure is wherein containing (a) at least one direct dye of general formula (I), in which
R1, R2, R3, R4 represent—independently of one another—a methyl group or an ethyl group, and
R5, R6 represent—independently of one another—a hydrogen atom, a methyl group, or an ethyl group.

Furthermore, the direct dyes of general formula (I) bear the residues R7 and R8; the residues R7 and R8, too, may be the same or different. Preferably, R7 and R8 represent—independently of one another—a hydrogen atom, a $C_1$-$C_6$ alkyl group, or a $C_1$-$C_6$ alkoxy group. Especially preferably, Here, R9 may represent a hydrogen atom, a $C_1$-$C_6$ alkyl group, a halogen atom from the group consisting of chlorine, bromine, fluorine, or iodine, or a $C_1$-$C_6$ alkoxy group. Especially preferably, R9 represents a hydrogen atom.

Bright, garnet red colorations were obtained in particular if dyes of formula (I) where Y1 and Y2 both represent a nitrogen atom were used. Very especially preferred, therefore, are the dyes of formula (I) with which Y2 and Y2 both represent a nitrogen atom.

In another especially preferred embodiment, an agent according to the present disclosure is wherein containing (a) at least one direct dye of general formula (I), in which —Y1 and Y2 both represent a nitrogen atom.

The dyes of formula (I) according to the present disclosure entail dimeric azo dyes that are doubly positively charged. The two positive charges are neutralized by the anionic counterions X1 and X2. The dicationic organic part is responsible here for the blue coloring of the keratin fibers. The counterions X1 and X2 serve solely to maintain electrical neutrality, such that the exact nature of the counterions X1 and X2 does not play an essential role in obtaining the desired color result. Because the dye is used in a cosmetic agent, the counterions X1 and X2 must be physiologically acceptable. "Physiologically acceptable" signifies in this context being suitable for use in the cosmetic agent (i.e., for use on human hair and on human skin). X1 and X2 involve physiologically acceptable anions, preferably from the group consisting of chloride, bromide, iodide, methyl sulfate, methyl sulfonate, p-toluenesulfonate, acetate, hydrogen sulfate, ½ sulfate, or ½ tetrachlorozincate;

Chloride is understood to mean a Cl⁻ anion. Bromide is understood to mean a Br⁻ anion. Iodide is understood to mean an I⁻ anion. Methyl sulfate is understood to mean an anion $H_3COSO_4^-$. p-Toluenesulfonate is understood to mean an anion $H_3C(C_6H_4)SO_3^-$. Acetate is understood to mean $H_3CCOO^-$. Hydrogen sulfate is understood to mean an anion $HSO_4^-$.

½ sulfate is understood to mean a half-equivalent of the doubly negatively charged anion $SO_4^{2-}$. ½ tetrachlorozincate is understood to mean a half-equivalent of the doubly negatively charged anion $ZnCl_4^{2-}$. With sulfate and tetrachlorozincate, consequently, it is also possible and in accordance with the present disclosure when the dicationic dye of formula (I) is neutralized by an $SO_4^{2-}$ ion or by a $ZnCl_4^{2-}$ ion.

The group Q entails a group that links the two singly positively charged chromophores of the dye into the dimer. Q represents a group of formula (II), (III), (IV), or (V), $$*\text{---}(CH_2)n\text{---}* \quad (II)$$

$$*\text{---}(CH_2)m\text{---}O\text{---}(CH_2)p\text{---}* \quad (III)$$

$$*\text{---}(CH_2)m\text{---}O\text{---}(CH_2)p\text{---}O\text{---}(CH_2)q\text{---}* \quad (IV)$$

$$*\text{---}(CH_2)m\text{---}\underset{R_{10}}{N}\text{---}(CH_2)p\text{---}* \quad (V)$$

n represents an integer from 3 to 6;
m, p, q represent—each independently of one another—the number 2 or 3;
R10 represent a hydrogen atom, a $C_1$-$C_6$ alkyl group, a $C_2$-$C_6$ alkenyl group, or a hydroxy $C_2$-$C_6$ alkyl group.

The two positions marked with stars each represent here the linkage positions to the two N atoms of formula (I).

It has surprisingly been found that it is fundamentally important and essential to an exemplary embodiment of the present disclosure, in order to achieve an intense color result, for the connecting group Q linking the two azo chromophores together to have a chain length of at least 3 atoms. For this reason, n in formula (II) represents an integer not less than 3. The connecting group Q of formula (II) accordingly has at least 3 C atoms (i.e., entails a group having the minimum length —$CH_2$—$CH_2$—$CH_2$—).

In formula (III), m and p each represent an integer not less than 2, such that this connecting group overall has a chain length of at least 5 C and O atoms (i.e., entails a group having the minimum length —$CH_2$—$CH_2$—O—$CH_2$—$CH_2$—).

In formula (IV), m, p, and q each represent an integer not less than 2, such that this connecting group has, analogously, a chain length of at least 8 C and O atoms (i.e., entails a group having the minimum length —$CH_2$—$CH_2$—O—$CH_2$—$CH_2$—O—$CH_2$—$CH_2$—).

Analogously, in formula (V), m and p represent integers not less than 2, such that this connecting group has a chain length of at least 5 C and N atoms.

Within the context of comparative testing, it has been found that dimeric azo dyes of the principal type of formula (I) which, however, possess a linking group Q not according to the present disclosure, with a length of only 2 C atoms, have extremely poor color take-up performance into the keratin fibers.

Whereas intense colorations with deep orange-red, cherry red, or garnet red tones can be achieved with the dyes of formula (I) according to the present disclosure, colorations with analogous dimeric dyes that are linked via a shorter group Q with a chain length of only 2 C atoms lead to practically no color take-up whatsoever into the keratinous fibers.

Without the intention of being limited to one theory, the diffusion of the short-chain dimeric dyes into the keratinous fibers could possibly be adversely affected by a rigid geometry connected with the short linking chain Q and, as a result thereof, an unfavorable spatial conformation of the dye.

Within the group Q of formulae (II), (III), (IV), and (V), the best color results and most intense colorations were achieved with the group of formula (II).

In a very especially preferred embodiment, an agent according to the present disclosure is wherein containing (a) at least one direct dye of general formula (I), in which Q represents a group of formula (II), $$*\text{---}(CH_2)n\text{-}* \quad (II)$$

and
n each represents-independently of one another—an integer 3 to 6.

In an explicitly very especially preferred embodiment, an agent according to the present disclosure is wherein containing (a) at least one dye of general formula (I), in which Q represents a group of formula (II), $$*\text{---}(CH_2)n\text{-}* \quad (II)$$

and
n represents the number 3.

In another preferred embodiment, an agent for dyeing keratinous fibers is wherein containing at least one compound of general formula (I) selected from:
salts of 2-[2-(4-{[3-({4-[2-(1,3-dimethyl-1H-imidazol-3-ium-2-yl)diazen-1-yl]phenyl)amino]propyl}amino)phenyl]diazen-1-yl]-1,3-dimethyl-1H-imidazol-3-ium salts of 2-[2-(4-{[4-({4[2-(1,3-dimethyl-1H-imidazol-3-ium-2-yl)diazen-1-yl]phenyl]-amino}butyl)amino]phenyl}diazen-1-yl]-1,3-dimethyl-1H-imidazol-3-ium

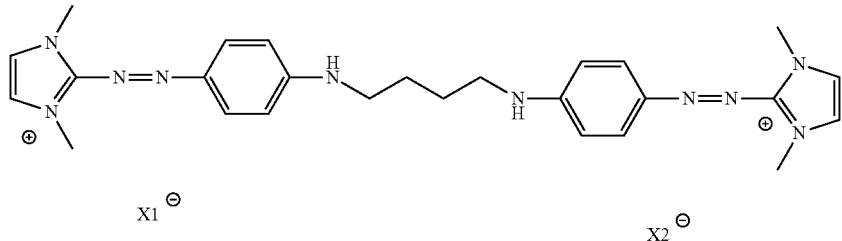

salts of 2-[2-(4-{[5-({4[2-(1,3-dimethyl-1H-imidazol-3-ium-2-yl)diazen-1-yl]phenyl}amino)pentyl]amino phenyl)diazen-1-yl]-1,3-dimethyl-1H-imidazol-3-ium

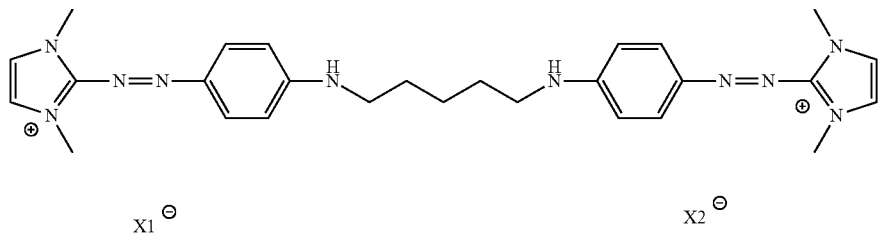

salts of 2-[2-(4-{[3-({4[2-(1,3-dimethyl-1H-imidazol-3-ium-2-yl)diazen-1-yl]phenyl}-(methyl)amino)propyl](methyl)amino}phenyl)diazen-1-yl]-1,3-dimethyl-1H-imidazol-3-ium

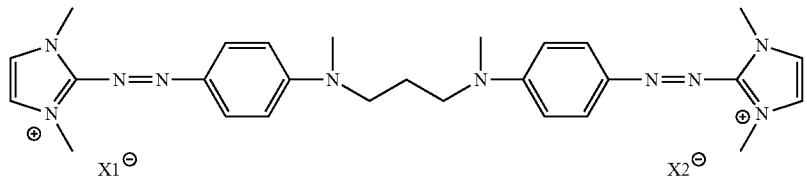

salts of 2-[2-(4-{[4-({4[2-(1,3-dimethyl-1H-imidazol-3-ium-2-yl)diazen-1-yl]phenyl}-(methyl)amino)butyl](methyl)amino}phenyl)diazen-1-yl]-1,3-dimethyl-1H-imidazol-3-ium

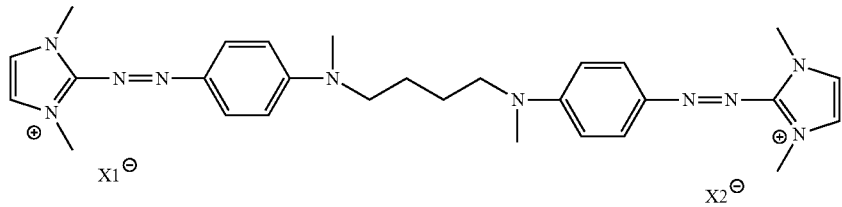

salts of 2-[2-(4-{[5-({4[2-(1,3-dimethyl-1H-imidazol-3-ium-2-yl)diazen-1-yl]phenyl}-(methyl)amino)pentyl](methyl)amino}phenyl)diazen-1-yl]-1,3-dimethyl-1H-imidazol-3-ium

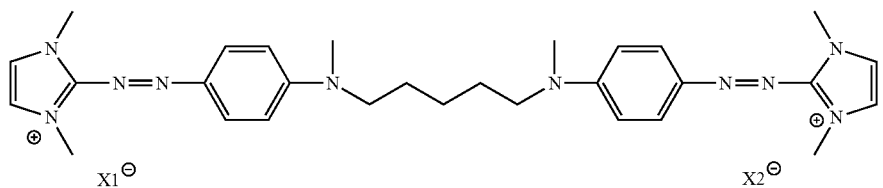

salts of 2-[2-(4-{[3-({4[2-(1,3-dimethyl-1H-imidazol-3-ium-2-yl)diazen-1-yl]phenyl}-(ethyl)amino)propyl](ethyl)amino}phenyl)diazen-1-yl]-1,3-dimethyl-1H-imidazol-3-ium

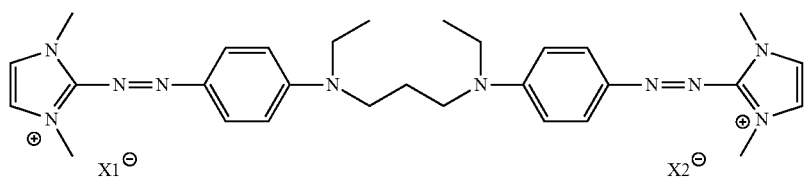

salts of 2-[2-(4-{[4-({4[2-(1,3-dimethyl-1H-imidazol-3-ium-2-yl)diazen-1-yl]phenyl}-(ethyl)amino)butyl](ethyl)amino}phenyl)diazen-1-yl]-1,3-dimethyl-1H-imidazol-3-ium

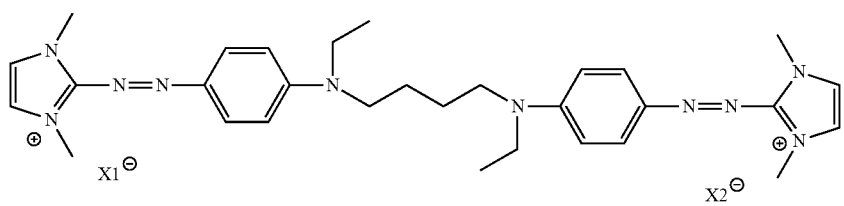

salts of 2-[2-(4-{[5-({4[2-(1,3-dimethyl-1H-imidazol-3-ium-2-yl)diazen-1-yl]phenyl]-(ethyl)amino}pentyl)(ethyl)amino}phenyl)diazen-1-yl]-1,3-dimethyl-1H-imidazol-3-ium

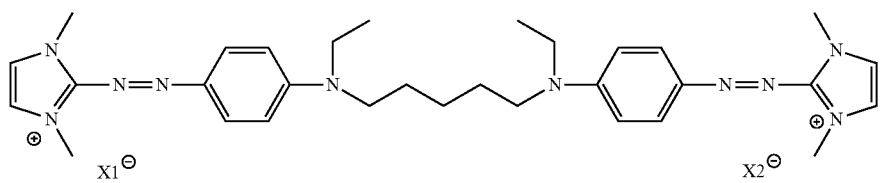

salts of 2-[2-(4-{[3-({4-[2-(1,3-diethyl-1H-imidazol-3-ium-2-yl)diazen-1-yl]phenyl}amino)propyl]amino}phenyl)diazen-1-yl]-1,3-diethyl-1H-imidazol-3-ium

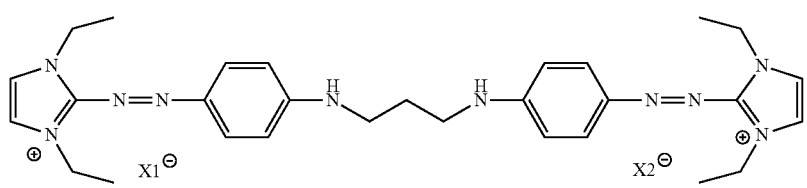

salts of 2-[2-(4-{[4-({4-[2-(1,3-diethyl-1H-imidazol-3-ium-2-yl)diazen-1-yl]phenyl}amino)-butyl]amino}phenyl)diazen-1-yl]-1,3-diethyl-1H-imidazol-3-ium

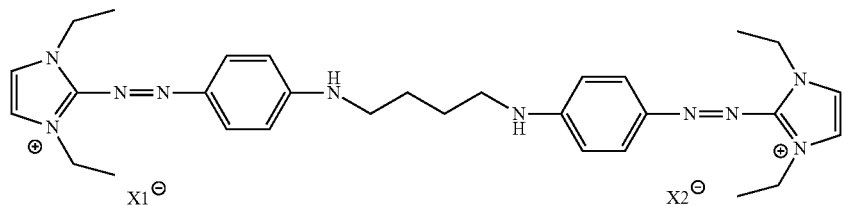

salts of 2-[2-(4-{[5-({-[2-(1,3-diethyl-1H-imidazol-3-ium-2-yl]diazen-1-yl]phenyl]-amino)pentyl]amino}phenyl)diazen-1-yl]-1,3-diethyl-1H-imidazol-3-ium

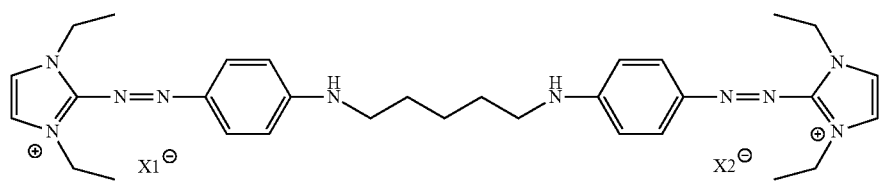

salts of 2-[2-(4-{[3-({4-[2-(1,3-diethyl-1H-imidazol-3-ium-2-yl)diazen-1-yl)phenyl]-(methyl)amino}propyl]methyl}amino)phenyl]diazen-1-yl]-1,3-diethyl-1H-imidazol-3-ium

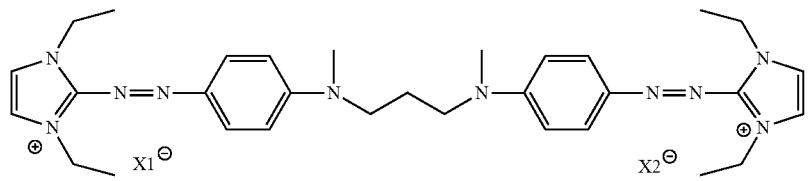

salts of 2-[2-(4-{[4-({4-[2-(1,3-diethyl-1H-imidazol-3-ium-2-yl)diazen-1-yl)phenyl]-(methyl)amino}butyl](methyl)amino}phenyl)diazen-1-yl]-1,3-diethyl-1H-imidazol-3-ium

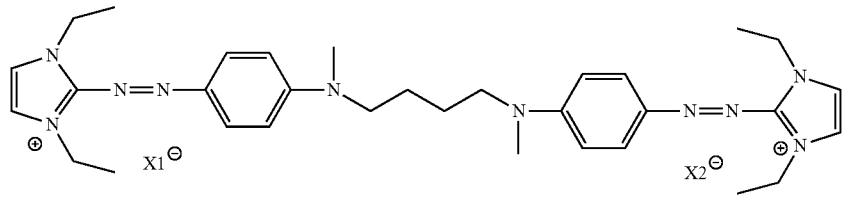

salts of 2-[2-(4-{[5-({4[2-(1,3-diethyl-1H-imidazol-3-ium-2-yl)diazen-1-yl]phenyl}-(methyl)amino)pentyl]methyl}amino}phenyl)diazen-1-yl]-1,3-diethyl-1H-imidazol-3-ium

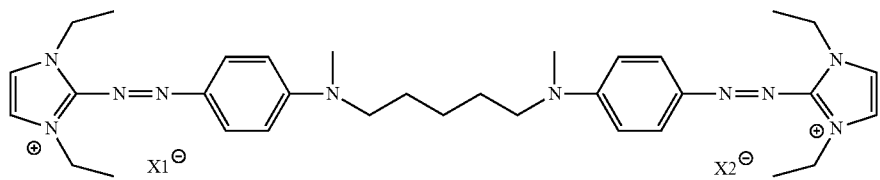

salts of 2-[2-(4-{[3-({4[2-(1,3-diethyl-1H-imidazol-3-ium-2-yl)diazen-1-yl]phenyl]-(ethyl)amino}propyl)(ethyl)amino}phenyl)diazen-1-yl]-1,3-diethyl-1H-imidazol-3-ium

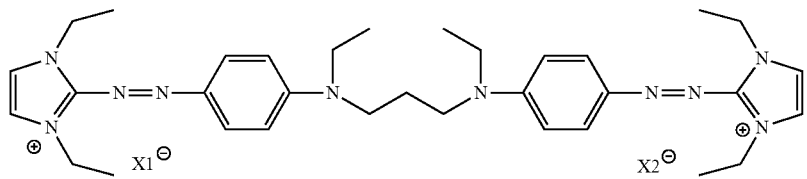

salts of 2-[2-(4-{[4-({4-[2-(1,3-diethyl-1H-imidazol-3-ium-2-yl)diazen-1-yl]phenyl)-(ethyl)amino}butyl](ethyl)amino}phenyl)diazen-1-yl]-1,3-diethyl-1H-imidazol-3-ium

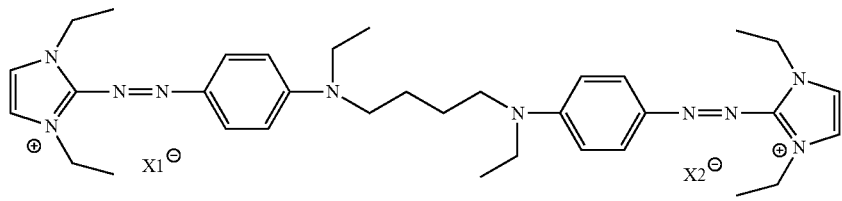

salts of 2-[2-(4-{[5-({4-[2-(1,3-diethyl-1H-imidazol-3-ium-2-yl)diazen-1-yl]phenyl]-(ethyl)amino}pentyl)(ethyl)amino}phenyl)diazen-1-yl]-1,3-diethyl-1H-imidazol-3-ium

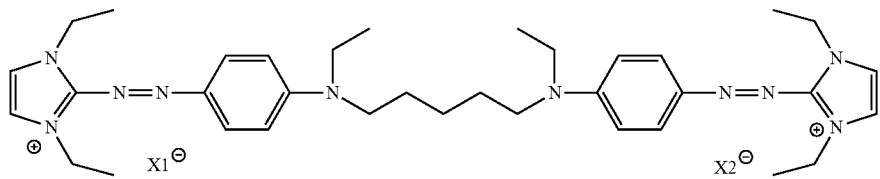

salts of 2-{2-[4-({2-[2-({4-[2-(1,3-dimethyl-1H-imidazol-3-ium-2-yl)diazen-1-yl]phenyl}amino)ethoxy]ethyl}amino)phenyl]diazen-1-yl}-1,3-dimethyl-1H-imidazol-3-ium

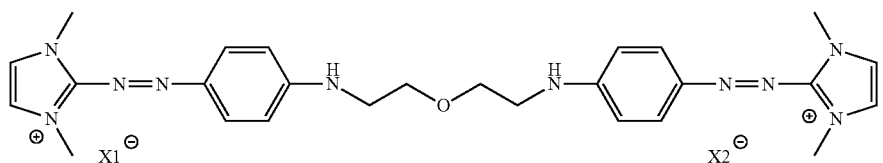

salts of 2-{2-[4-({2-[2-({4[2-(1,3-dimethyl-1H-imidazol-3-ium-2-yl)diazen-1-yl]phenyl]-(methyl)amino)ethoxy]ethyl}(methyl)amino)phenyl]diazen-1-yl}-1,3-dimethyl-1H-imidazol-3-ium

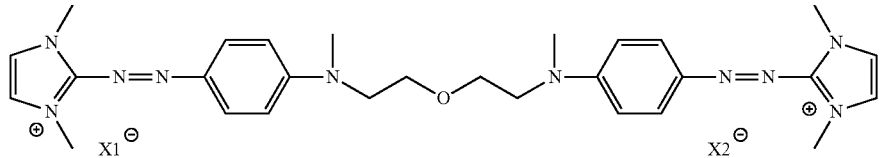

salts of 2-{2-[4-({2-[2-({4[2-(1,3-dimethyl-1H-imidazol-3-ium-2-yl)diazen-1-yl]phenyl}-(ethyl)amino)ethoxy)ethyl}(ethyl)amino)phenyl]diazen-1-yl}-1,3-dimethyl-1H-imidazol-3-ium

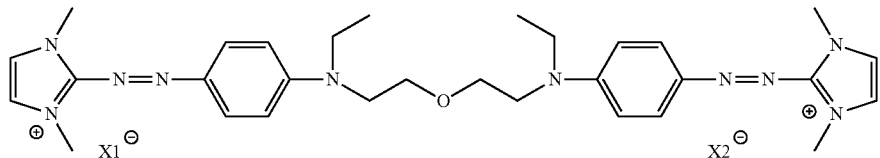

salts of 2-{2-[4-({2-[2-({4[2-(1,3-diethyl-1H-imidazol-3-ium-2-yl)diazen-1-yl]phenyl]-amino}ethoxy)ethyl}amino)phenyl]diazen-1-yl}-1,3-diethyl-1H-imidazol-3-ium

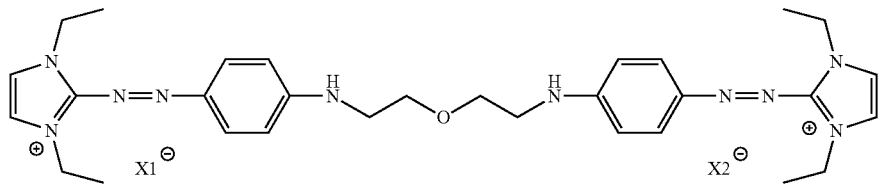

salts of 2-{2-[4-({2-[2-({4-[2-(1,3-diethyl-1H-imidazol-3-ium-2-yl)diazen-1-yl]phenyl}-(methyl)amino)ethoxy]ethyl}(methyl)amino)phenyl]diazen-1-yl}-1,3-diethyl-1H-imidazol-3-ium

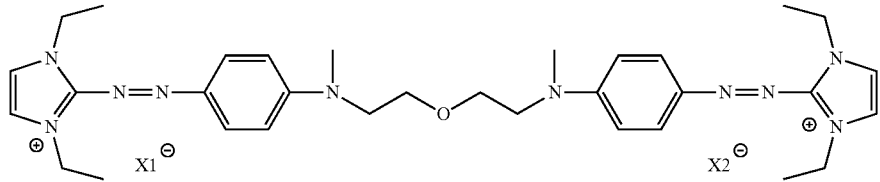

salts of 2-{2-[4-({2-[2-({4-[2-(1,3-diethyl-1H-imidazol-3-ium-2-yl)diazen-1-yl]phenyl}-(ethyl)amino)ethoxy]ethyl}(ethyl)amino)phenyl]diazen-1-yl}-1,3-diethyl-1H-imidazol-3-ium

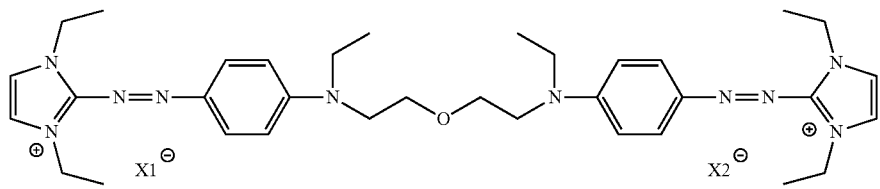

salts of 5-[2-(4-{[3-({4[2-(1,4-dimethyl-1H-1,2,4-triazol-4-ium-5-yl)diazen-1-yl]phenyl}amino)propyl]amino}phenyl)diazen-1-yl]-1,4-dimethyl-1H-1,2,4-triazol-4-ium

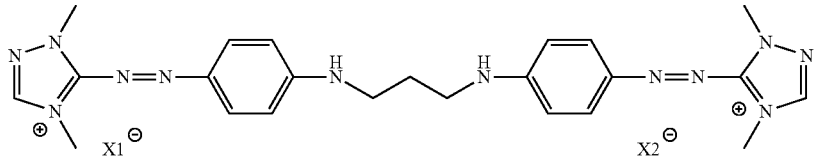

salts of 5-[2-(4-{[4-({4-[2-(1,4-dimethyl-1H-1,2,4-triazol-4-ium-5-yl)diazen-1-yl]phenyl}amino)butyl]amino}phenyl)diazen-1-yl]-1,4-dimethyl-1H-1,2,4-triazol-4-ium

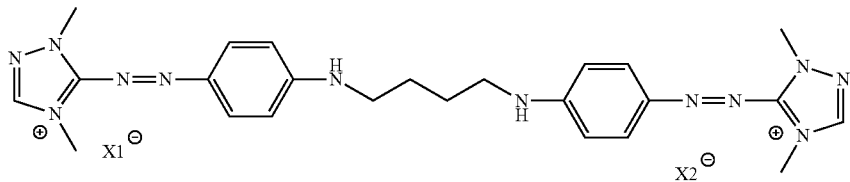

salts of 5-[2-(4-{[5-({4-[2-(1,4-dimethyl-1H-1,2,4-triazol-4-ium-5-yl)diazen-1-yl]phenyl}amino)pentyl]amino}phenyl)diazen-1-yl]-1,4-dimethyl-1H-1,2,4-triazol-4-ium

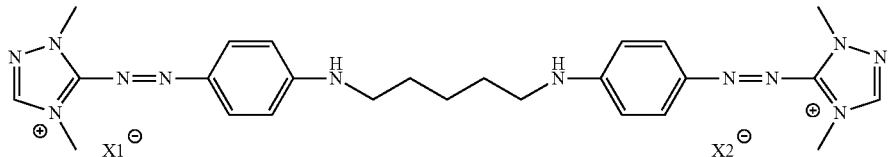

salts of 5-[2-(4-{[3-({4[2-(1,4-dimethyl-1H-1,2,4-triazol-4-ium-5-yl)diazen-1-yl]phenyl}-(methyl)amino)propyl](methyl)amino}phenyl)diazen-1-yl]-1,4-dimethyl-1H-1,2,4-triazol-4-ium

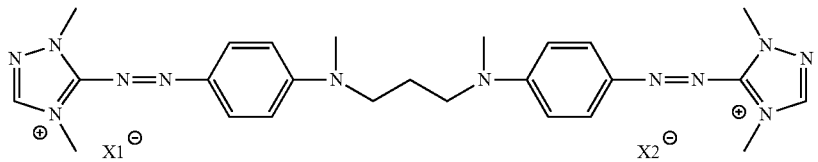

salts of 5 [2-(4-{[4-({4-[2-(1,4-dimethyl-1H-1,2,4-triazol-4-ium-5-yl)diazen-1-yl]phenyl]-(methyl)amino}butyl)(methyl)amino}phenyl)diazen-1-yl]-1,4-dimethyl-1H-1,2,4-triazol-4-ium

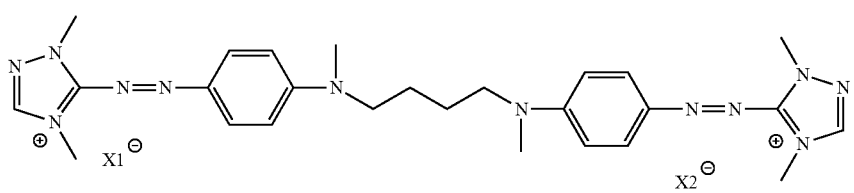

salts of 5-[2-(4-{[5-({4[2-(1,4-dimethyl-1H-1,2,4-triazol-4-ium-5-yl)diazen-1-yl]phenyl}-(methyl)amino)pentyl](methyl)amino}phenyl)diazen-1-yl]-1,4-dimethyl-1H-1,2,4-triazol-4-ium

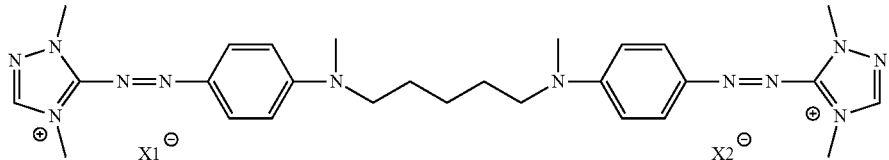 [SMILES: CN(CCCCCN(C)c1ccc(N=Nc2n(C)nc[n+]2C)cc1)c1ccc(N=Nc2n(C)nc[n+]2C)cc1 ; "X1" ; "X2"]

salts of 5-[2-(4-{[3-({4[2-(1,4-dimethyl-1H-1,2,4-triazol-4-ium-5-yl)diazen-1-yl]phenyl]-(ethyl)amino}propyl)(ethyl)amino}phenyl)diazen-1-yl]-1,4-dimethyl-1H-1,2,4-triazol-4-ium

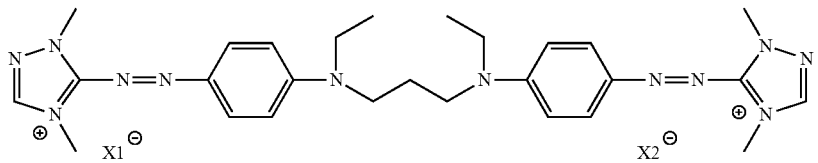

salts of 5-[2-(4-{[4-({4[2-(1,4-dimethyl-1H-1,2,4-triazol-4-ium-5-yl)diazen-1-yl]phenyl}-(ethyl)amino)butyl](ethyl)amino}phenyl)diazen-1-yl]-1,4-dimethyl-1H-1,2,4-triazol-4-ium

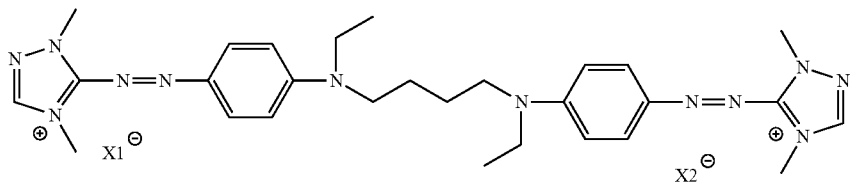

salts of 5-[2-(4-{[5-({4-[2-(1,4-dimethyl-1H-1,2,4-triazol-4-ium-5-yl)diazen-1-yl]phenyl}-(ethyl)amino)pentyl](ethyl)amino}phenyl)diazen-1-yl]-1,4-dimethyl-1H-1,2,4-triazol-4-ium

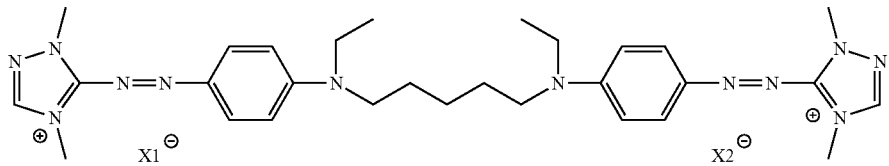 [SMILES: CCN(CCCCCN(CC)c1ccc(N=Nc2n(C)nc[n+]2C)cc1)c1ccc(N=Nc2n(C)nc[n+]2C)cc1 ; "X1" ; "X2"]

salts of 5-[2-(4-{[3-({4-[2-(1,4-diethyl-1H-1,2,4-triazol-4-ium-5-yl)diazen-1-yl]phenyl}-amino)propyl]amino}phenyl)diazen-1-yl]-1,4-diethyl-1H-1,2,4-triazol-4-ium

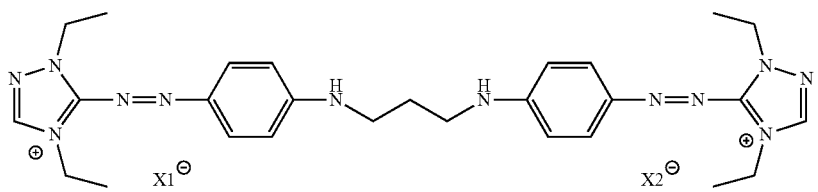

salts of 5-[2-(4-{[4-({4-[2-(1,4-diethyl-1H-1,2,4-triazol-4-ium-5-yl)diazen-1-yl]phenyl]-amino)butyl]amino}phenyl)diazen-1-yl]-1,4-diethyl-1H-1,2,4-triazol-4-ium

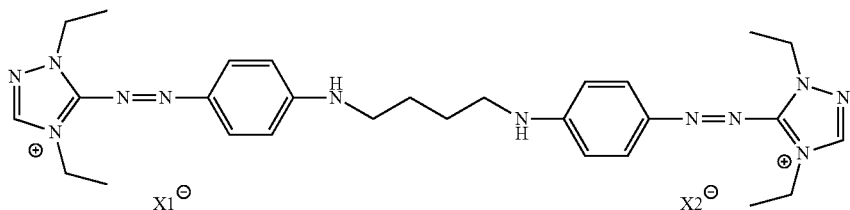

salts of 5-[2-(4-{[5-({4-[2-(1,4-diethyl-1H-1,2,4-triazol-4-ium-5-yl)diazen-1-yl]phenyl}amino)pentyl]amino}phenyl)diazen-1-yl]-1,4-diethyl-1H-1,2,4-triazol-4-ium

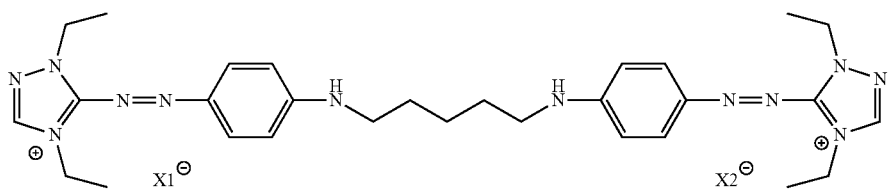

salts of 5-[2-(4-{[3-({4[2-(1,4-diethyl-1H-1,2,4-triazol-4-ium-5-yl)diazen-1-yl]phenyl}-(methyl)amino)propyl](methyl)amino}phenyl)diazen-1-yl]-1,4-diethyl-1H-1,2,4-triazol-4-ium

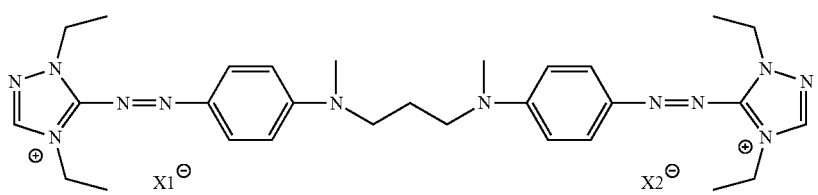

salts of 5-[2-(4-{[4-({4[2-(1,4-diethyl-1H-1,2,4-triazol-4-ium-5-yl)diazen-1-yl]phenyl}-(methyl)amino)butyl](methyl)amino}phenyl)diazen-1-yl]-1,4-diethyl-1H-1,2,4-triazol-4-ium

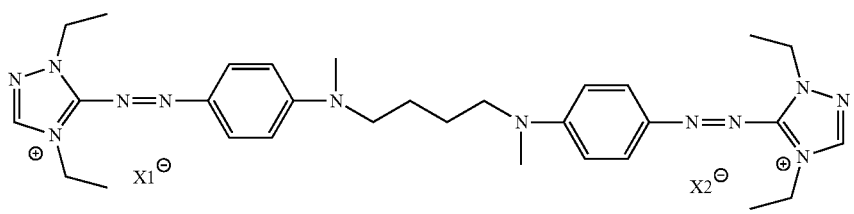

salts of 5-[2-(4-{[5-({4-[2-(1,4-diethyl-1H-1,2,4-triazol-4-ium-5-yl)diazen-1-yl]phenyl}-(methyl)amino)pentyl](methyl)amino}phenyl)diazen-1-yl]-1,4-diethyl-1H-1,2,4-triazol-4-ium

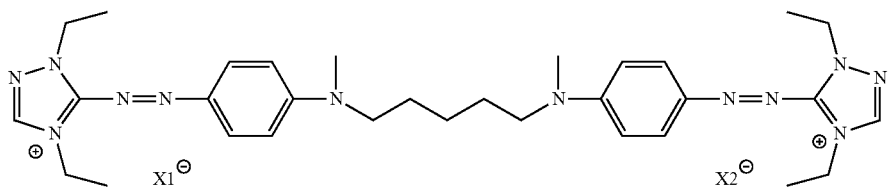

salts of 5-[2-(4-{[3-({4[2-(1,4-diethyl-1H-1,2,4-triazol-4-ium-5-yl)diazen-1-yl]phenyl]-(ethyl)amino}propyl)(ethyl)amino}phenyl)diazen-1-yl)-1,4-diethyl-1H-1,2,4-triazol-4-ium

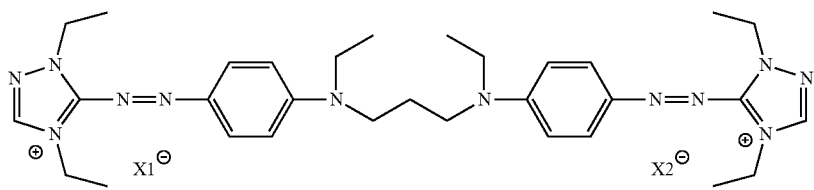

salts of 5-[2-(4-{[4-({4[2-(1,4-diethyl-1H-1,2,4-triazol-4-ium-5-yl)diazen-1-yl]phenyl}-(ethyl)amino)butyl](ethyl)amino}phenyl)diazen-1-yl]-1,4-diethyl-1H-1,2,4-triazol-4-ium

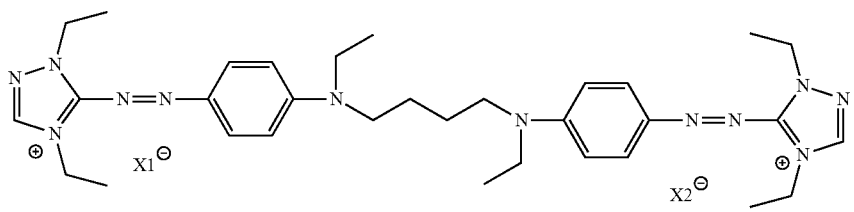

salts of 5-[2-(4-{[5-({4[2-(1,4-diethyl-1H-1,2,4-triazol-4-ium-5-yl)diazen-1-yl]phenyl}-(ethyl)amino)pentyl](ethyl)amino}phenyl)diazen-1-yl]-1,4-diethyl-1H-1,2,4-triazol-4-ium

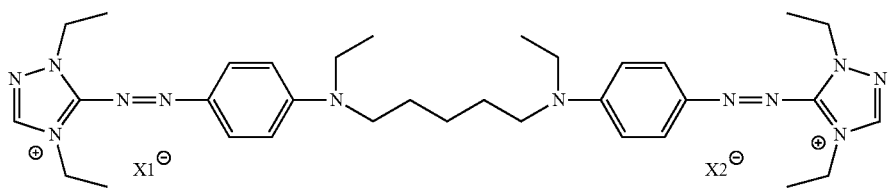

salts of 5-{2-[4-({2-[2-({4-[2-(1,4-dimethyl-1H-1,2,4-triazol-4-ium-5-yl)diazen-1-yl]phenyl}amino)ethoxy]ethyl}amino)phenyl]diazen-1-yl}-1,4-dimethyl-1H-1,2,4-triazol-4-ium

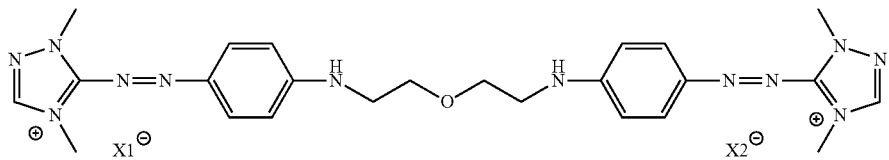

salts of 5-{2-[4-({2-[2-({4[2-(1,4-dimethyl-1H-1,2,4-triazol-4-ium-5-yl)diazen-1-yl]phenyl}-(ethyl)amino)ethoxy]ethyl}(methyl)amino)phenyl]diazen-1-yl}-1,4-dimethyl-1H-1,2,4-triazol-4-ium

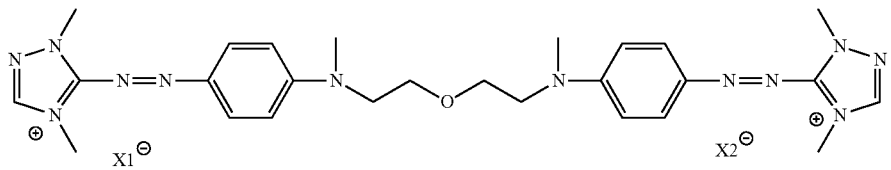

salts of 5-{2-[4-({2-[2-({4-[2-(1,4-diethyl-1H-1,2,4-triazol-4-ium-5-yl)diazen-1-yl]phenyl}(ethyl)amino)ethoxy]ethyl}(ethyl)amino)phenyl]diazen-1-yl}-1,4-dimethyl-1H-1,2,4-triazol-4-ium

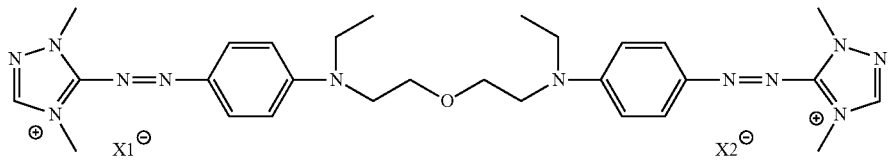

salts of 5-{2-[4-({2-[2-({4[2-(1,4-diethyl-1H-1,2,4-triazol-4-ium-5-yl)diazen-1-yl]phenyl}-amino)ethoxy)ethyl{amino}phenyl)diazen-1-yl]-1,4-diethyl-1H-1,2,4-triazol-4-ium

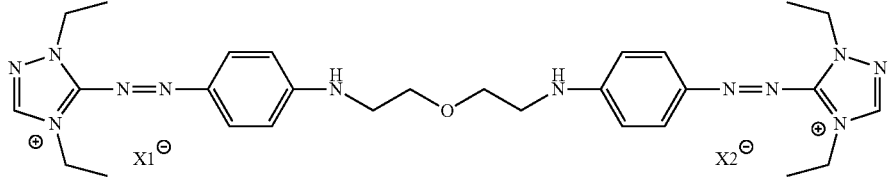

salts of 5-(2-[4-({2-[2-({4-[2-(1,4-diethyl-1H-1,2,4-triazol-4-ium-5-yl)diazen-1-yl]phenyl}1-(methyl)amino)ethoxy]ethyl](methyl)amino}phenyl}diazen-1-yl}-1,4-diethyl-1H-1,2,4-triazol-4-ium

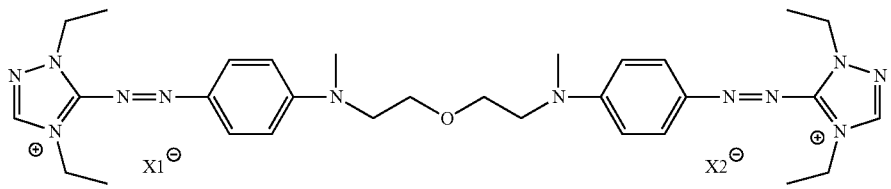

salts of 5-{2-[4-({2-[2-({4[2-(1,4-diethyl-1H-1,2,4-triazol-4-ium-5-yl)diazen-1-yl]phenyl}-(ethyl)amino)ethoxy]ethyl) (ethyl)amino)phenyl]diazen-1-yl}-1,4-diethyl-1H-1,2,4-triazol-4-ium

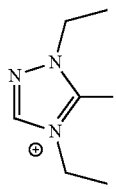 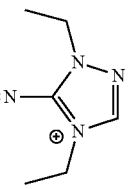

The aforementioned compounds entail dicationic dimeric dyes, wherein the organic dication is neutralized by the two anions X1- and X2-. The anions X1- and X2 each involve a physiologically acceptable anion, preferably from the group consisting of chloride, bromide, iodide, methyl sulfate, methyl sulfonate, p-toluenesulfonate, acetate, hydrogen sulfate, ½ sulfate, or ½ tetrachlorozincate;

In an especially preferred embodiment, an agent according to the present disclosure for dyeing keratinous fibers is wherein containing, as the dye of formula (a), at least one compound selected from the group consisting of:

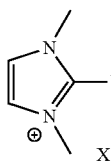 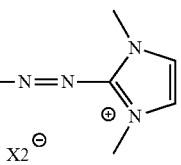

2-[2-(4-{[3-((4[2-(1,3-Dimethyl-1H-imidazol-3-ium-2-yl)diazen-1-yl]phenyl}amino)propyl]amino}-phenyl)diazen-1-yl]-1,3-dimethyl-1H-imidazol-3-ium dichloride 2-[2-(4-{[3-((4[2-(1,3-Dimethyl-1H-imidazol-3-ium-2-yl)diazen-1-yl]phenyl}amino)propyl]amino}-phenyl)diazen-1-yl]-1,3-dimethyl-1H-imidazol-3-ium dibromide 2-[2-(4-{[3-({4[2-(1,3-Dimethyl-1H-imidazol-3-ium-2-yl)diazen-1-yl]phenyl]amino)propyl]aminol-phenyl)diazen-1-yl]-1,3-dimethyl-1H-imidazol-3-ium sulfate 2-[2-(4-{[3-({(4[2-(1,3-Dimethyl-1H-imidazol-3-ium-2-yl)diazen-1-yl]phenyl}amino)propyl]amino}-phenyl)diazen-1-yl]-1,3-dimethyl-1H-imidazol-3-ium di(toluenesulfonate)

2-[2-(4-{[3-({(4[2-(1,3-Dimethyl-1H-imidazol-3-ium-2-yl)diazen-1-yl]phenyl}amino)propyl]amino}-phenyl)diazen-1-yl]-1,3-dimethyl-1H-imidazol-3-ium di(methyl sulfate)

2-[2-(4-{[3-({4 [2-(1,3-Dimethyl-1H-imidazol-3-ium-2-yl)diazen-1-yl]phenyl]amino)propyl]aminol-phenyl)diazen-1-yl]-1,3-dimethyl-1H-imidazol-3-ium tetrachlorozincate 2-[2-(4-{[3-({(4[2-(1,3-Dimethyl-1H-imidazol-3-ium-2-yl)diazen-1-yl]phenyl}(methyl)amino)propyl]-(methyl)amino}phenyl)diazen-1-yl]-1,3-dimethyl-1H-imidazol-3-ium dichloride 2-[2-(4-{[3-({(4[2-(1,3-Dimethyl-1H-imidazol-3-ium-2-yl)diazen-1-yl]phenyl}(methyl)amino)propyl]-(methyl)amino}phenyl)diazen-1-yl]-1,3-dimethyl-1H-imidazol-3-ium dibromide 2-[2-(4-{[3-({4[2-(1,3-Dimethyl-1H-imidazol-3-ium-2-yl)diazen-1-yl]phenyl](methyl)amino)propyl]-(methyl)amino}phenyl)diazen-1-yl]-1,3-dimethyl-1H-imidazol-3-ium sulfate 2-[2-(4-{[3-({4[2-(1,3-Dimethyl-1H-imidazol-3-ium-2-yl)diazen-1-yl]phenyl}(methyl)amino)propyl]-(methyl)amino}phenyl)diazen-1-yl]-1,3-dimethyl-1H-imidazol-3-ium di(toluenesulfonate)

2-[2-(4-{[3-({4[2-(1,3-Dimethyl-1H-imidazol-3-ium-2-yl)diazen-1-yl]phenyl}(methyl)amino)propyl]-(methyl)amino}phenyl}diazen-1-yl)-1,3-dimethyl-1H-imidazol-3-ium di(methyl sulfate)

2-[2-(4-{[3-({4[2-(1,3-Dimethyl-1H-imidazol-3-ium-2-yl)diazen-1-yl]phenyl}(methyl)amino)propyl]-(methyl)amino}phenyl)diazen-1-yl]-1,3-dimethyl-1H-imidazol-3-ium tetrachlorozincate

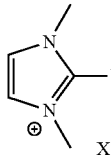 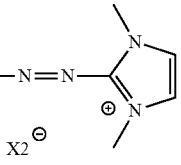

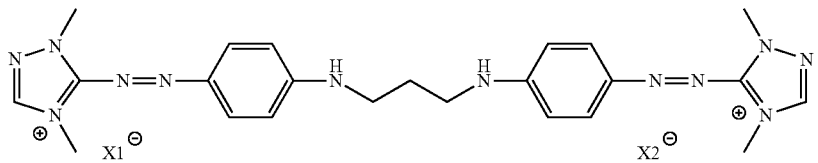

5-[2-(4-{[3-({4-[2-(1,4-Dimethyl-1H-1,2,4-triazol-4-ium-5-yl)diazen-1-yl]phenyl]amino)propyl]-amino}phenyl}diazen-1-yl)-1,4-dimethyl-1H-1,2,4-triazol-4-ium dichloride 5-[2-(4-{[3-({4-[2-(1,4-Dimethyl-1H-1,2,4-triazol-4-ium-5-yl)diazen-1-yl]phenyl}amino)propyl]-amino)phenyl)diazen-1-yl]-1,4-dimethyl-1H-1,2,4-triazol-4-ium dibromide 5-[2-(4-{[3-({4-[2-(1,4-Dimethyl-1H-1,2,4-triazol-4-ium-5-yl)diazen-1-yl]phenyl]amino)propyl]-amino}phenyl)diazen-1-yl]-1,4-dimethyl-1H-1,2,4-triazol-4-ium sulfate 5-[2-(4-{[3-({4-[2-(1,4-Dimethyl-1H-1,2,4-triazol-4-ium-5-yl)diazen-1-yl]phenyl}amino)propyl]-amino}phenyl)diazen-1-yl)-1,4-dimethyl-1H-1,2,4-triazol-4-ium di(toluenesulfonate)

5-[2-(4-{[3-({4-[2-(1,4-Dimethyl-1H-1,2,4-triazol-4-ium-5-yl)diazen-1-yl]phenyl}amino)propyl]-amino}phenyl]diazen-1-yl]-1,4-dimethyl-1H-1,2,4-triazol-4-ium di(methyl sulfate)

5-[2-(4-{[3-({4-[2-(1,4-Dimethyl-1H-1,2,4-triazol-4-ium-5-yl)diazen-1-yl]phenyl]amino)propyl]-amino}phenyl)diazen-1-yl]-1,4-dimethyl-1H-1,2,4-triazol-4-ium tetrachlorozincate 5-[2-(4-{[3-({4-[2-(1,4-Dimethyl-1H-1,2,4-triazol-4-ium-5-yl)diazen-1-yl]phenyl}(methyl)amino)propyl]-(methyl)amino]phenyl]diazen-1-yl]-1,4-dimethyl-1H-1,2,4-triazol-4-ium di(methyl sulfate)

5-[2-(4-{[3-({4-[2-(1,4-Dimethyl-1H-1,2,4-triazol-4-ium-5-yl)diazen-1-yl]phenyl](methyl)amino)propyl]-(methyl)amino}phenyl)diazen-1-yl]-1,4-dimethyl-1H-1,2,4-triazol-4-ium tetrachlorozincate.

The agents according to the present disclosure for dyeing keratinous fibers preferably contain the direct dye(s) of formula (I) in a total amount of about 0.01 to about 4.5% by weight, preferably about 0.05 to about 2.8% by weight, further preferably about 0.1 to about 2.2% by weight, and especially preferably about 0.2 to about 1.2% by weight. The amounts set forth in percent by weight refer here to the total amount of all compounds of formula (I) contained in the agent, relative to the total weight of the agent.

In another preferred embodiment, an agent according to the present disclosure for dyeing keratinous fibers is therefore wherein containing—relative to the total weight of the agent—one or more direct dyes (a) of formula (I) in a total amount of about 0.01 to about 4.5% by weight, preferably about 0.05 to about 2.8% by weight, further preferably about 0.1 to about 2.2% by weight, and especially preferably about 0.2 to about 1.2% by weight.

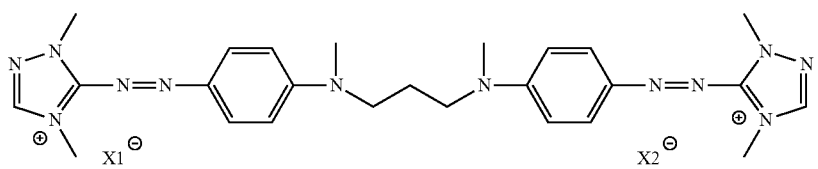

5-[2-(4-{[3-({4-[2-(1,4-Dimethyl-1H-1,2,4-triazol-4-ium-5-yl)diazen-1-yl]phenyl](methyl)amino)propyl]-(methyl)amino}phenyl)diazen-1-yl]-1,4-dimethyl-1H-1,2,4-triazol-4-ium dichloride 5-[2-(4-{[3-({4-[2-(1,4-Dimethyl-1H-1,2,4-triazol-4-ium-5-yl)diazen-1-yl]phenyl}(methyl)amino)propyl]-(methyl)amino}phenyl)diazen-1-yl]-1,4-dimethyl-1H-1,2,4-triazol-4-ium dibromide 5-[2-(4-{[3-({4-[2-(1,4-Dimethyl-1H-1,2,4-triazol-4-ium-5-yl)diazen-1-yl]phenyl}(methyl)amino)propyl]-(methyl)amino}phenyl)diazen-1-yl]-1,4-dimethyl-1H-1,2,4-triazol-4-ium sulfate 5-[2-(4-{[3-({4-[2-(1,4-Dimethyl-1H-1,2,4-triazol-4-ium-5-yl)diazen-1-yl]phenyl}(methyl)amino)propyl]-(methyl)amino]phenyl]diazen-1-yl}-1,4-dimethyl-1H-1,2,4-triazol-4-ium di(toluenesulfonate)

The dyes of general formula (I) may be prepared, for example, in a manner analogous to methods described in WO 2002/100369 A2.

Thus, for example, the reactant 3-amino-1,2,4-triazole may be converted into the diazonium ion in concentrated sulfuric acid with nitrosylsulfuric acid.

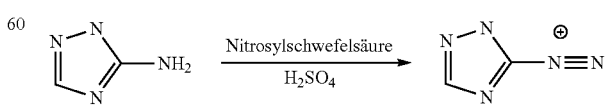

The reactive diazonium ion then takes part in a doubled azo coupling reaction with dimeric aniline derivatives:

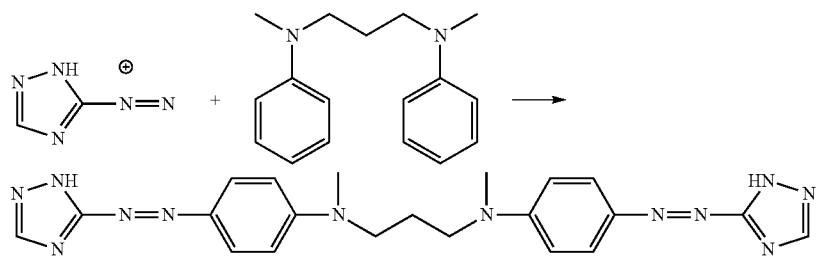

The neutral dimeric dye resulting from the azo coupling reaction may then be quaternized with quaternizing agents and thus converted into the dicationic form. The quaternization reaction is preferably performed in a polar aprotic solvent (e.g., DMSO, DMF, etc.). Examples of possible quaternizing agents include dimethyl sulfate, methyl bromide, or p-toluenesulfonate.

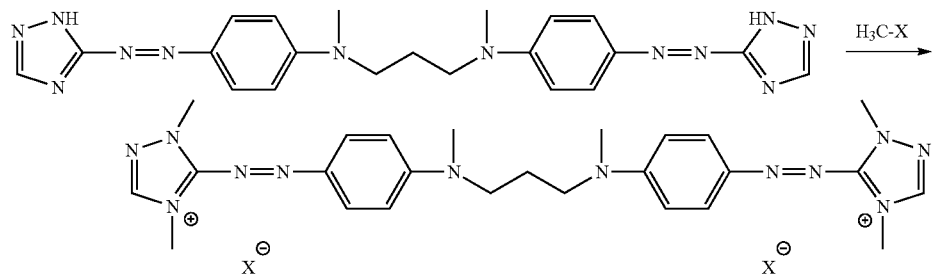

As the second component (b) that is essential to the present disclosure, the agents for dyeing keratinous fibers contain at least one anionic surfactant and/or at least one cationic surfactant Surfactants are amphiphilic (bifunctional) compounds composed of at least one hydrophobic moiety and at least one hydrophilic moiety. The hydrophobic residue is preferably a hydrocarbon chain including 8 to 24 carbon atoms, which may be saturated or unsaturated, linear or branched. This $C_8$ to $C_{24}$ alkyl chain is particularly preferably linear.

With anionic surfactants, the hydrophilic moiety comprises a negatively charged hydrophilic head group. The negatively charged hydrophilic head group may entail, for example, a carboxylic acid group or the salt of a carboxylic acid group, a sulfonic acid group or the salt of the sulfonic acid group, a sulfuric acid ester group or the salt thereof, a phosphonic acid group or the salt of the phosphonic acid group, or a phosphoric acid ester group or the salt thereof.

The cosmetic agent according to the present disclosure commonly contains an aqueous carrier. In the aqueous solution, the aforementioned hydrophilic head groups of the anionic surfactant—e.g., the carboxylic acid and the salts of the carboxylic acids—are in equilibrium, the position of which is determined by the pH value of the agent. If, therefore, for example, a fatty acid is used as the anionic surfactant, then a small part of the fatty acid in the aqueous solution is present in the form of the protonated fatty acid, whereas most of the fatty acid in the aqueous solution is deprotonated and thus is converted into the salt of the fatty acid. For this reason, the definition of an anionic surfactant also encompasses a surfactant that has one still-protonated acid group.

An anionic surfactant (b) within the meaning of the present disclosure does not contain any cationic groups, i.e., zwitterionic surfactants are not covered by the definition of an anionic surfactant.

Anionic surfactants according to the present disclosure are accordingly wherein the presence of a water-solubilizing anionic group, such as a carboxylate, sulfate, sulfonate, or phosphate group, and a lipophilic alkyl group having about 8 to 30 C atoms. In addition, glycol or polyglycol ether groups, ester, ether, amide, and hydroxyl groups may be contained in the molecule. Typical examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (in particular, wheat-based vegetable products), and alkyl(ether) phosphates. If the anionic surfactants contain polyglycol ether chains, they may have a conventional homolog distribution although they preferably have a narrow-range homolog distribution.

Examples of anionic surfactants according to the present disclosure—each example being in the form of the corresponding sodium, potassium, ammonium, or mono-, di-, or trialkanolammonium salt thereof having 2 to 4 C atoms in the alkanol group—are:

linear and branched fatty acids having 8 to 30 C atoms (soaps);

ether carboxylic acids of the formula $R-O-(CH_2-CH_2O)_x-CH_2-COOH$, in which R is a linear alkyl group having 8 to 30 C atoms and $x=0$ or 1 to 16;

acyl sarcosides having 8 to 24 C atoms in the acyl group;
acyl taurides having 8 to 24 C atoms in the acyl group;

acyl isethionates having 8 to 24 C atoms in the acyl group that can be obtained by esterification of fatty acids with the sodium salt of 2-hydroxyethane sulfonic acid (isethionic acid). If fatty acids having 8 to 24 C atoms, e.g., lauric acid, myristic acid, palmitic acid, or stearic acid, or industrial fatty acid fractions, e.g., the $C_{12}$-$C_{18}$ fatty acid fractions that can be obtained from coconut fatty acid are used for this esterification, $C_{12}$-$C_{18}$ acyl isethionates that are preferably suitable according to the present disclosure are used.

sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups; The sulfosuccinic acid mono- and dialkyl esters are produced by reacting maleic anhydride with a fatty alcohol having 8 to 24 C atoms to form the maleic acid monoester of the fatty alcohol and further reacting with sodium sulfite to form the sulfosuccinic acid ester. Especially suitable sulfosuccinic acid esters are derived from fatty alcohol fractions having 12 to 18 C atoms, such as can be obtained, e.g., from coconut fatty acid or coconut fatty acid methyl esters by hydrogenation.

linear alkane sulfonates having 8 to 24 C atoms;
linear α-olefin sulfonates having 8 to 24 C atoms;
α-sulfo fatty acid methyl esters of fatty acids having 8 to 30 C atoms;
alkylsulfates and alkyl polyglycol ether sulfates of the formula R—O(CH$_2$—CH$_2$O)$_x$—OSO$_3$H, in which R is a preferably linear alkyl group having 8 to 30 C atoms and x=0 or 1 to 12.

hydroxysulfonates substantially corresponding to at least one of the two following formulae, or mixtures thereof, or salts thereof: CH$_3$—(CH$_2$)$_y$—CHOH—(CH$_2$)$_p$—(CH—SO$_3$M)-(CH$_2$)$_z$—CH$_2$—O—(C$_n$H$_{2n}$O)$_x$—H, and/or CH$_3$—(CH$_2$)$_y$—(CH—SO$_3$M)-(CH$_2$)$_p$—CHOH—(CH$_2$)$_z$—CH$_2$—O—(C$_n$H$_{2n}$O)$_x$—H, wherein—in both formulae—y and z=0 or integers from 1 to 18, p=0, 1, or 2 and the sum (y+z+p) is a number from 12 to 18, x=0 or a number from 1 to 30, and n is an integer from 2 to and 4, and M=H or an alkali ion, in particular, a sodium, potassium, lithium, alkaline earth metal, especially magnesium, calcium, zinc and/or ammonium ion which may optionally be substituted, in particular, mono-, di-, tri-, or tetraammonium ions having C1 to C4 alkyl, alkenyl, or aryl residues, sulfated hydroxyalkyl polyethylene and/or hydroxyalkylene propylene glycol ethers, of the formula R$^1$—(CHOSO$_3$M)-CHR$^3$—(OCHR$^4$—CH$_2$)$_n$—OR$^2$ in which R$^1$ stands for a linear alkyl residue having 1 to 24 C atoms, R$^2$ for a linear or branched, saturated alkyl residue having 1 to 24 C atoms, R$^3$ for hydrogen or a linear alkyl residue having 1 to 24 C atoms, R$^4$ for hydrogen or a methyl group, and M for hydrogen, ammonium, alkylammonium, alkanolammonium, where the alkyl and alkanol groups each have 1 to 4 C atoms, or a metal atom selected from lithium, sodium, potassium, calcium, or magnesium, and n for a number in the range of about 0 to 12, and furthermore the total number of C atoms in R$^1$ and R$^3$ is 2 to 44, sulfonates of unsaturated fatty acids having 8 to 24 C atoms and 1 to 6 double bonds, esters of tartaric acid and citric acid with alcohols, which represent addition products of about 2-15 molecules ethylene oxide and/or propylene oxide to fatty alcohols having 8 to 22 C atoms, alkyl and/or alkenyl ether phosphates of the formula R$^1$(OCH$_2$CH$_2$)$_n$—O—(PO—OX)—OR$^2$,
in which R$^1$ preferably stands for an aliphatic hydrocarbon group having 8 to 30 carbon atoms, R$^2$ for hydrogen, a group (CH$_2$CH$_2$O)$_n$R$^2$, or X, n for numbers from 1 to 10, and X for hydrogen, an alkali metal or alkaline earth metal or NR$^3$R$^4$R$^5$R$^{6'}$ where R$^3$ to R$^6$ independently of one another stand for hydrogen or a C1 to C4 hydrocarbon group, sulfated fatty acid alkylene glycol esters of the formula RCO(AlkO)$_n$SO$_3$M in which RCO— stands for a linear or branched, aliphatic, saturated and/or unsaturated acyl residue having 6 to 22 C atoms, Alk for CH$_2$CH$_2$, CHCH$_3$CH$_2$, and/or CH$_2$CHCH$_3$, n for numbers from 0.5 to 5, and M for a metal, such as an alkali metal, particularly sodium, potassium, lithium, alkaline earth metal, particularly magnesium, calcium, zinc, or ammonium ion, such as $^+$NR$^3$R$^4$R$^5$R$^6$, whereby R$^3$ to R$^6$ independently of one another stand for hydrogen or a C1 to C4 hydrocarbon group, monoglyceride sulfates and monoglyceride ether sulfates of the formula R$^8$OC—(OCH$_2$CH$_2$)$_x$—OCH$_2$—[CHO(CH$_2$CH$_2$O)$_y$H]—CH$_2$O(CH$_2$CH$_2$O)$_z$—SO$_3$X, in which R$^8$CO stands for a linear or branched acyl residue having 6 to 22 carbon atoms, x, y, and z in total for 0 or for numbers from 1 to 30, preferably 2 to 10, and X for an alkali or alkaline earth metal. Typical examples within the meaning of the present disclosure for suitable monoglyceride (ether) sulfates are the reaction products of lauric acid monoglyceride, coconut fatty acid monoglyceride, palmitic acid monoglyceride, stearic acid monoglyceride, oleic acid monoglyceride, and tallow fatty acid monoglyceride, as well as the ethylene oxide adducts thereof with sulfur trioxide or chlorosulfonic acid in the form of the sodium salts there. Preferably, monoglyceride sulfates are used in which R$^8$CO stands for a linear acyl residue having 8 to 18 carbon atoms, amide ether carboxylic acids, R$^1$—CO—NR$^2$—CH$_2$CH$_2$—O—(CH$_2$CH$_2$O)$_n$CH$_2$COOM, with R$^1$ as a straight-chain or branched alkyl or alkenyl residue with a number of carbon atoms in the chain of 2 to 30, n stands for an integer from 1 to 20, and R$^2$ stands for hydrogen, a methyl, ethyl, propyl, isopropyl, n-butyl, t-butyl, or isobutyl residue, and M stands for hydrogen or a metal such as an alkali metal, particularly sodium, potassium, lithium, alkaline earth metal, particularly magnesium, calcium, zinc, or an ammonium ion, such as $^+$NR$^3$R$^4$R$^5$R$^6$, whereby R$^3$ to R$^6$ independently of one another stand for hydrogen or a C1 to C4 hydrocarbon group. Such products can be obtained, for example, from the company Chem-Y under the product name Akypo®, and acyl glutamates of the formula XOOC—CH$_2$CH$_2$CH(C(NH)OR)—COOX, in which RCO stands for a linear or branched acyl residue having 6 to 22 carbon atoms and 0 and/or 1, 2, or 3 double bonds and X for hydrogen, an alkali and/or alkaline earth metal, ammonium, alkyl ammonium, alkanol ammonium, or glucammonium.

Treating keratinous fibers with agents that contain (a) at least one direct dye of formula (I) and (b) at least one anionic surfactant led to intense colorations in attractive, pure shades of blue without reddishness. Here, it has surprisingly been found that the color take-up performance could be still further optimized by using one or more specific anionic surfactants. Especially intense blue colorations were obtained when the dyes (a) of formula (I) with at least one anionic surfactant (b) from the group consisting of:

linear and branched fatty acids having 8 to 30 C atoms;
ether carboxylic acids of the formula R—O—(CH$_2$—CH$_2$O)$_x$—CH$_2$—COOH, in which R is a linear alkyl group having 8 to 30 C atoms and x=0 or 1 to 16;
acyl sarcosides having 8 to 24 C atoms in the acyl group;
acyl taurides having 8 to 24 C atoms in the acyl group;
acyl isethionates having 8 to 24 C atoms in the acyl group that can be obtained by esterification of fatty acids with the sodium salt of 2-hydroxyethane sulfonic acid (isethionic acid). If fatty acids having 8 to 24 C atoms, e.g., lauric acid, myristic acid, palmitic acid, or stearic acid, or industrial fatty acid fractions, e.g., the $C_{12}$-$C_{18}$ fatty acid fractions that can be obtained from coconut fatty acid are used for this esterification, $C_{12}$-$C_{18}$ acyl isethionates that are preferably suitable according to the present disclosure are used.

amide ether carboxylic acids, $R^1$—CO—$NR^2$—$CH_2CH_2$—O—$(CH_2CH_2O)_n CH_2 COOM$, with R1 as a straight-chain or branched alkyl or alkenyl residue with a number of carbon atoms in the chain of 2 to 30, n stands for an integer from 1 to 20, and R2 stands for hydrogen, a methyl, ethyl, propyl, isopropyl, n-butyl, t-butyl, or isobutyl residue, and M stands for hydrogen or a metal such as an alkali metal, particularly sodium, potassium, lithium, alkaline earth metal, particularly magnesium, calcium, zinc, or an ammonium ion, such as $^+NR^3R^4R^5R^6$, whereby $R^3$ to $R^6$ independently of one another stand for hydrogen or a C1 to C4 hydrocarbon group. Such products can be obtained, for example, from the company Chem-Y under the product name Akypo®, and acyl glutamates of the formula XOOC—CH2CH2CH(C(NH)OR)—COOX, in which RCO stands for a linear or branched acyl residue having 6 to 22 carbon atoms and 0 and/or 1, 2, or 3 double bonds and X for hydrogen, an alkali and/or alkaline earth metal, ammonium, alkyl ammonium, alkanol ammonium, or glucammonium.

In an especially preferred embodiment, an agent according to the present disclosure is therefore wherein containing (b) at least one anionic surfactant selected from:

linear and branched fatty acids having 8 to 30 C atoms;
ether carboxylic acids of formula R—O—$(CH_2$—$CH_2O)_x$—$CH_2$—COOM, in which
R represents a linear alkyl group having 8 to 30 C atoms,
x represents an integer from 0 to 16,
M represents hydrogen or a metal such as an alkali metal, in particular, sodium, potassium, or lithium, an alkaline-earth metal, in particular, ½ magnesium, ½ calcium, ½ zinc, or an ammonium ion ($NH_4^+$);

acyl sarcosides having 8 to 24 C atoms in the acyl group;
acyl taurides having 8 to 24 C atoms in the acyl group;
acyl isethionates having 8 to 24 C atoms in the acyl group that can be obtained by esterification of $C_8$-$C_{24}$ fatty acids with the sodium salt of 2-hydroxyethane sulfonic acid (isethionic acid), amide ether carboxylic acids, $R^1$—CO—$NR^2$—$CH_2CH_2$—O—$(CH_2CH_2O)_y CH_2 COOM$, wherein
$R^1$ represents a $C_2$-$C_{30}$ alkyl group,
y represents an integer from 1 to 20,
$R^2$ represents hydrogen or a methyl, ethyl, propyl, isopropyl, n-butyl, t-butyl, or isobutyl residue; and
M represents hydrogen or a metal such as an alkali metal, in particular, sodium, potassium, or lithium, an alkaline earth metal, in particular, ½ magnesium, ½ calcium, ½ zinc, or an ammonium ion ($NH_4^+$), An especially favorable color take-up performance could be observed when (b) at least one ether carboxylic acid of formula R—O—$(CH_2$—$CH_2O)_x$—$CH_2$—COOH or a salt thereof was used as the anionic surfactant. The use of (optionally ethoxylated) ether carboxylic acids is therefore explicitly very especially preferred.

In an explicitly very especially preferred embodiment, an agent according to the present disclosure is therefore wherein containing, as the anionic surfactant, (b) at least one ether carboxylic acid of formula (B1)

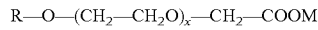

(B1), wherein
R represents a linear alkyl group having 8 to 30 C atoms,
x represents an integer from 0 to 16,
M represents hydrogen or a metal such as an alkali metal, in particular, sodium, potassium, or lithium, an alkaline earth metal, in particular, magnesium, calcium, zinc, or an ammonium ion ($NH_4^+$); Further especially preferably, x represents an integer from 5 to 11, very especially preferably for the numbers 5, 6, or 7.

In a furthermore very especially preferred embodiment, an agent according to the present disclosure is therefore wherein containing, as the anionic surfactant, (b) at least one ether carboxylic acid of formula (B1)

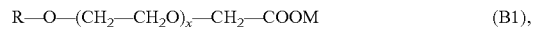

wherein
R represents a linear alkyl group having 8 to 30 C atoms,
x represents an integer from 5 to 11,
M represents hydrogen or a metal such as an alkali metal, in particular, sodium, potassium, or lithium, an alkaline earth metal, in particular, magnesium, calcium, zinc, or an ammonium ion ($NH_4^+$);

The very especially preferred anionic surfactants of formula (B1) can be obtained, for example, under the trade names Akypo Soft 45 HP, from the company Kao (sodium laureth-6 carboxylate)
Akypo Soft 45 NV, from the company Kao (sodium laureth-5 carboxylate)
Akypo RLM 100 NV, from the company Kao (sodium laureth-11 carboxylate)

The agents according to the present disclosure for dyeing keratinous fibers preferably contain one or more anionic surfactants (b) in a total amount of about 0.05 to about 4.5% by weight, preferably about 0.1 to about 2.1% by weight, further preferably about 0.15 to about 1.8% by weight, and very especially preferably about 0.2 to about 0.9% by weight. Here, the amounts set forth in percent by weight refer to the total amount of all of the anionic surfactants (b), relative to the total amount of the dye.

In another especially preferred embodiment, an agent according to the present disclosure for dyeing keratinous fibers is therefore wherein containing—relative to the total weight of the agent—one or more anionic surfactants (b) in a total amount of about 0.05 to about 4.5% by weight, preferably about 0.1 to about 3.1% by weight, further preferably about 0.15 to about 2.5% by weight, and very especially preferably about 0.2 to about 0.9% by weight.

As previously described, it has been shown that varying the anionic surfactant(s) (b) makes it possible to influence the color take-up performance of the direct dyes of formula (I).

In general, the color take-up can be improved by using at least one anionic surfactant. Using at least one—optionally ethoxylated—ether carboxylic acid and/or a salt thereof, such as described in formula (B1), has proven to be especially advantageous in this context. In this context, it has been observed that the keratin fibers could be dyed can then be dyed with especially intense red shades when the ether carboxylic acid(s) (and/or salts thereof) was/were contained in the agent according to the present disclosure as the main anionic surfactant.

In other words, the dyeing results were especially intense when the agents according to the present disclosure contained one or more ether carboxylic acids of formula (B1), and when, in addition, all other anionic surfactants that were used were present only in smaller quantities. The use of the ether carboxylic acid(s) of formula (B1) as the main surfactant can be quantified by specifying a weight ratio that sets the total amount of the anionic surfactants of formula (B1) contained in the agent in relation to the total amount of all of the anionic surfactants (b) contained in the agent.

In another especially preferred embodiment, an agent according to the present disclosure for dyeing keratinous fibers is characterized in that the weight ratio of all of the anionic surfactants of formula (B1) contained in the agent to the total amount of anionic surfactants contained in the agent is at a value of about 0.5, preferably about 0.6, further preferably about 0.75, and especially preferably about 0.9.

Example

An agent for dyeing keratinous fibers contains:
(a) 1.0 g 5-[2-(4-{[3-({4[2-(1,4-Dimethyl-1H-1,2,4-triazol-4-ium-5-yl)diazen-1-yl]phenyl}(methyl)amino)-propyl](methyl)amino}phenyl)diazen-1-yl]-1,4-dimethyl-1H-1,2,4-triazol-4-ium tetrachlorozincate
(b) 0.23 g sodium laureth-6 carboxylate (B1), and
(b) 0.10 g sodium laureth sulfate (2 EO)
The weight ratio of all of the anionic surfactants of formula (B1) contained in the agent to the total amount of the anionic surfactants contained in the agent is at a value of [0.23/(0.23+0.1)]=0.69.

Example

An agent for dyeing keratinous fibers contains:
(a) 1.0 g 5-[2-(4-{[3-({4[2-(1,4-Dimethyl-1H-1,2,4-triazol-4-ium-5-yl)diazen-1-yl]phenyl}(methyl)amino)-propyl](methyl)amino}phenyl)diazen-1-yl]-1,4-dimethyl-1H-1,2,4-triazol-4-ium di(methyl sulfate)
(b) 0.23 g sodium laureth-6 carboxylate (B1)
The weight ratio of all of the anionic surfactants of formula (B1) contained in the agent to the total amount of the anionic surfactants contained in the agent is at a value of [0.23/0.23]=1.0.

The second component (b) that is essential according to the present disclosure may also entail a cationic surfactant. When the dyes of formula (I) according to the present disclosure were applied in combination with at least one cationic surfactant, it was also possible to achieve colorations with a greatly-improved color take-up and enhanced color intensity.

"Cationic surfactants" are understood to mean surfactants—i.e., surface-active compounds—that each have one or more positive charges. Cationic surfactants have exclusively positive charges. Generally, these surfactants are composed of a hydrophobic part and a hydrophilic head group, wherein the hydrophobic part is generally composed of a hydrocarbon skeleton (for example, composed of one or two linear or branched alkyl chains), and the positive charge(s) in the hydrophilic head group is/are localized. Cationic surfactants adsorb and interfaces and aggregate in an aqueous solution above the critical micelle-forming concentration to form positively charged micelles.

Examples of cation surfactants include
quaternary ammonium compounds, which may bear one or two alkyl chains having a chain length of 8 to 28 C atoms as hydrophobic residues;
quaternary phosphonium salts, substituted with one or more alkyl chains having a chain length of 8 to 28 C atoms; or
tertiary sulfonium salts.

Furthermore, the cationic charge may also be in the form of an onium structure component of a heterocyclic ring (for example, an imidazolium ring or a pyridinium ring).

In addition to the functional unit bearing the cationic charge, the cation surfactant may also include other uncharged functional groups; this is the case, for example, with Esterquats. Within the group of cationic surfactants (b), an improved color take-up and therewith an enhanced color intensity could be achieved, in particular, with the cationic ammonium compounds of formula (B2). The cationic surfactants of formula (B2) are therefore especially preferred,

wherein
Ra, Rb represent—independently of one another—a $C_1$-$C_6$ alkyl group, a $C_2$-$C_6$ alkenyl group, or a $C_2$-$C_6$ hydroxyalkyl group;
Rc represents a $C_1$-$C_7$ alkyl group, a $C_8$-$C_{28}$ alkyl group, a $C_2$-$C_6$ alkenyl group, or a $C_2$-$C_6$ hydroxyalkyl group;
Rd represents a $C_8$-$C_{28}$ alkyl group, and
$X^-$ represents a physiologically acceptable anion.

In another preferred embodiment, a product according to the present disclosure is therefore wherein containing, as (a) cationic surfactant(s) (c), one or more compounds of formula (I),

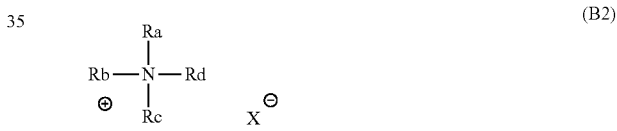

wherein
Ra, Rb represent—independently of one another—a $C_1$-$C_6$ alkyl group, a $C_2$-$C_6$ alkenyl group, or a $C_2$-$C_6$ hydroxyalkyl group;
Rc represents a $C_1$-$C_7$ alkyl group, a $C_8$-$C_{28}$ alkyl group, a $C_2$-$C_6$ alkenyl group, or a $C_2$-$C_6$ hydroxyalkyl group;
Rd represents a $C_8$-$C_{28}$ alkyl group, and
$X^-$ represents a physiologically acceptable anion.

The substituents Ra, Rb, Rc, and Rd of the compound of formula (B2) are explained by way of example below: Examples of a $C_1$-$C_6$ alkyl group are the methyl, ethyl, propyl, isopropyl, n-butyl, s-butyl, and t-butyl, n-pentyl, and n-hexyl groups. Propyl, ethyl, and methyl are preferred alkyl residues. Examples of a $C_2$-$C_6$ alkenyl group are vinyl, allyl, but-2-enyl, but-3-enyl, and isobutenyl, preferred $C_2$-$C_6$ alkenyl residues being vinyl and allyl. Preferred examples of a hydroxy $C_1$-$C_6$ alkyl group are a hydroxymethyl, 2-hydroxyethyl, 2-hydroxypropyl, 3-hydroxypropyl, 4-hydroxybutyl, 5-hydroxypentyl, and 6-hydroxyhexyl group, a 2-hydroxyethyl group being particularly preferred.

Preferably, Ra and Rb represent—independently of one another—a $C_1$-$C_6$ alkyl group. It is especially preferred when Ra and Rb represent—independently of one another—a methyl group, an ethyl group, or an n-propyl group. In a very especially preferred embodiment Ra and Rb both represent a methyl group or both represent an ethyl group.

Rd and optionally Rc present a $C_8$-$C_{28}$ alkyl group. These alkyl groups may be branched or unbranched, saturated or unsaturated. If unsaturated, the $C_8$-$C_{28}$ alkyl group may be mono- or polyunsaturated, i.e., have one or more double bonds.

Preferably, Rc represents a $C_1$-$C_7$ alkyl group. Very especially preferably, Rc represents a methyl group, an ethyl group, or a propyl group, in particular, a methyl group.

If Rd represents a linear saturated $C_{16}$-$C_{22}$ alkyl group, this has a very especially advantageous effect on the properties of the foam caused by spraying. Preferably, therefore, R4 represents a linear saturated $C_{16}$-$C_{22}$ alkyl group. It is very especially preferable when R4 represents a linear saturated $C_{20}$ alkyl group or a linear saturated $C_{22}$ alkyl group.

In another very especially preferred embodiment, a product according to the present disclosure is therefore wherein containing, as (a) cationic surfactant(s) (c), one or more compounds of formula (B2),

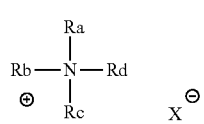

wherein
Ra, Rb represent—independently of one another—a $C_1$-$C_6$ alkyl group, preferably both representing a methyl group;
Rc represents a methyl group, an ethyl group, or a propyl group, preferably a methyl group; and
Rd represents a $C_{16}$-$C_{22}$ alkyl group, preferably a $C_{20}$ alkyl group or a $C_{22}$ alkyl group;
$X^-$ represents a physiologically acceptable anion.

Preferred cationic surfactants of formula (I) are, for example, physiologically acceptable salts of N,N,N-trimethyl-1-hexadecanaminium, in particular, N,N,N-trimethyl-1-hexadecanaminium chloride, which is marked under the trade name Dehyquart A-CA. Also preferred are salts of trimethylstearyl ammonium, in particular, trimethylstearyl ammonium chloride, which is commercially available under the trade name Genamin STAC.

Additionally especially preferred cationic surfactants of formula (I) are salts of trimethyl-1-eicosanaminium, in particular, trimethyl-1-eicosanaminium chloride, and salts of trimethyl-1-docosan-aminium, in particular, trimethyl-1-docosanaminium chloride. A mixture of both compounds is available under the trade name Genamin KDMP from the company Olariant.

$X^-$ in formula (B2) represents a physiologically acceptable anion. Suitable physiologically acceptable anions are halide, hydrogen sulfate, sulfate, benzenesulfonate, p-toluenesulfonate, acetate, citrate, lactate, tartrate, methyl sulfate ($H_3COSO_3^-$), methyl sulfonate, or trifluoromethane sulfonate. Especially preferably, $A^-$ represents chloride, bromide, or methyl sulfate ($H_3COSO_3^-$).

Other cationic surfactants may be selected from the group of cationic imidazolium compounds.

The agents according to the present disclosure may contain the cationic surfactant(s) in a total amount of about 0.1 to about 4.8% by weight, preferably about 0.2 to about 2.4% by weight, further preferably about 0.3 to about 1.8% by weight, relative to the total weight of the agent.

In another preferred embodiment, a product according to the present disclosure is therefore wherein containing one or more cationic surfactants (b) in a total amount of about 0.1 to about 4.8% by weight, preferably about 0.2 to about 2.4% by weight, further preferably about 0.3 to about 1.8% by weight, relative to the total weight of the agent.

It has furthermore proven advantageous when the agents contain other non-ionogenic surface-active substances. Alkyl polyglycosides and alkylene oxide addition products with fatty alcohols and fatty acids having (in each case) 2 to 30 mol ethylene oxide per mol fatty alcohol/fatty acid have proven to be preferred non-ionic surfactants. Preparations having excellent properties are also obtained when said preparations contain fatty acid esters of ethoxylated glycerol as non-ionic surfactants.

The non-ionic, zwitterionic, or amphoteric surfactants are used in proportions of about 0.1 to about 45% by weight, preferably about 1 to about 30% by weight, and very especially preferably about 1 to about 15% by weight, relative to the total amount of the application-ready agent.

In another preferred embodiment, the agents according to the present disclosure additionally contain at least one other direct dye, in addition to the compound of formula (I). Combining with other cationic direct dyes makes it possible to broaden the achievable spectrum of shades, and still further improve the dyeing properties.

Direct dyes can be divided into anionic, cationic, and non-ionic direct dyes.

The direct dyes are preferably selected from the cationic direct dyes, because these are favorably compatible with the dyes of general formula (I).

In another especially preferred embodiment, an agent according to the present disclosure is wherein additionally containing at least one other cationic direct dye that is different from the dyes of formula (I).

One or more dyes from the group consisting of Basic Yellow 87, Basic Orange 31, Basic Red 51, Basic Violet 2, and Cationic Blue 347 have proven to be especially favorably compatible.

Dyes of formula (I) are very especially favorable compatible with the cationic azo dyes Basic Orange 31 and Basic Red 51.

In another especially preferred embodiment, an agent according to the present disclosure is wherein additionally containing Basic Orange 31 and/or Basic Red 51.

The agent according to the present disclosure may also, however, additionally contain at least one non-ionic direct dye. These may be selected from the group: HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethy)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

It is possible to additionally include anionic direct dyes known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. The agents according to the present disclosure may furthermore also be used together with oxidation dyes. Such oxidation dyes additionally contain at least one oxidation dye precursor, preferably at least one oxidation dye precursor of the developer type and at least one oxidation dye precursor of the coupler type. Especially suitable oxidation dye precursors of the developer type are then selected from at least one compound from the group consisting of p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, Bis-(2-hydroxy-5-aminophenyl)-methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-Amino-3-methylphenol, 4-Amino-2-aminomethylphenol, 4-amino-2-(1,2-dihydroxyethyl)phenol, 4-amino-2-(diethylaminomethyl)-phenol, 4,5-diamino-1-(2-hydroxyethyl) pyrazol, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-on, and physiologically acceptable salts thereof.

Especially suitable oxidation dye precursors of the coupler type are selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)-amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl}amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or physiologically acceptable salts thereof.

The additional direct dyes, developer components, and coupler components are preferably used at a proportion of about 0.0001 to about 5.0% by weight, preferably about 0.001 to about 3.5% by weight, each relative to the application-ready agent. Then, developer components and coupler components are generally used at molar quantities to one another. When the molar usage has also proven useful, then a certain excess of individual oxidation dye precursors is not detrimental, such that developer components and coupler components may be in a molar ratio of about 1:0.5 to 1:3, in particular about 1:1 to 1:2.

Should the dyeing with the direct dyes of formula (I) according to the present disclosure and oxidative bleaching of the keratin fibers proceed in one step, then the agents according to the present disclosure additionally contain an oxidizing agent, preferably hydrogen peroxide and/or a solid addition product thereof with organic or inorganic compounds.

In a preferred embodiment, hydrogen peroxide is even used as an aqueous solution. The concentration of a hydrogen peroxide solution in the agent according to the present disclosure is determined by legal requirements on the one hand, and by the desired effect on the other; about 6- to about 12-wt % solutions in water are preferred. Application-ready agents of the first subject matter of the present disclosure that are preferred according to the present disclosure are wherein containing—relative to the total weight of the application-ready agent—about 0.5 to about 20% by weight, preferably about 1 to about 12.5% by weight, especially preferably about 2.5 to about 10% by weight, and, in particular, about 3 to about 6% by weight hydrogen peroxide, in each case relative to the total weight of the agent.

In another especially preferred embodiment, an agent according to the present disclosure is wherein containing— relative to the total weight of the agent—about 0.5 to about 12.5% by weight, preferably about 2.5 to about 10% by weight and, in particular, about 3 to about 6% by weight hydrogen peroxide.

To achieve an intensified lightening and bleaching action, the agent may furthermore contain at least one peroxo salt. Suitable peroxo salts are inorganic peroxo compounds, preferably selected from the group consisting of ammonium peroxodisulfates, alkali metal peroxodisulfates, ammonium peroxomonosulfates, alkali metal peroxomonosulfates, alkali metal peroxodiphosphates, and alkaline earth metal peroxides. Especially preferred are peroxodisulfates, in particular, ammonium peroxodisulfate, potassium peroxodisulfate, and sodium peroxodisulfate.

In another especially preferred embodiment, an agent according to the present disclosure is wherein additionally containing at least one persulfate from the group consisting of ammonium peroxodisulfate, potassium peroxodisulfate, and sodium peroxodisulfate.

The persulfates are each contained in the agent according to the present disclosure in a quantity of about 0.5 to about 20% by weight, preferably about 1 to about 12.5% by weight, especially preferably about 2.5 to about 10% by weight, and, in particular, about 3 to about 6% b weight, relative to the total weight of the application-ready agent.

The dyeing and/or matting agent may, in order to intensify the blonding action, contain other blonding power enhancers, e.g., tetraacetyl ethylenediamine (TAED), 1,5-diacetyl-2,4-dioxo-hexahydro-1,3,5-triazine (DADHT), tetraacetyl glycoluril (TAGU), N-nonanoyl succinimide (NOSI), n-nonanoyl- or isononanoyl oxybenzene sulfonate (n- or i-NOBS), phthalic anhydride, triacetin, ethylene glycol diacetate, and 2,5-diacetoxy-2,5-dihydrofuran, as well as carbonate salts or
hydrogen carbonate salts, in particular, ammonium hydrogen carbonate, ammonium carbonate, sodium hydrogen carbonate, disodium carbonate, potassium hydrogen carbonate, dipotassium carbonate, and calcium carbonate, and nitrogen-containing heterocyclic bleaching power enhancers such as 4-acetyl-1-methylpyridinium-p-toluenesulfonate, 2-acetyl-1-methylpyridinium-p-toluenesulfonate, and N-methyl-3,4-dihydroisochinolinium-p-toluenesulfonate.

To further increase the bleaching, at least one $SiO_2$ compound, e.g., silicic acid or silicates, in particular, soluble glasses may additionally be added to the composition according to the present disclosure. It may be preferred according to the present disclosure to use the $SiO_2$ compounds in amounts of about 0.05 to about 15% by weight, especially preferably in amounts of about 0.15 to about 10% by weight, and very especially preferably in amounts of about 0.2 to about 5% by weight, in each case relative to the anhydrous composition according to the present disclosure. The amounts specified then reflect in each case of the $SiO_2$ compound content (without the water content thereof) in the agents.

The dyes may furthermore contain additional active ingredients, auxiliaries, and additives, in order to improve the dyeing performance and adjust other desired properties of the agent.

Preferably, the dyes are prepared as a liquid preparation, and another surface-active substance is therefore optionally additionally added to the agents, wherein such surface-active substances are called surfactants or emulsifiers, depending on the field of use. They are preferably selected from anionic, zwitterionic, amphoteric, and non-ionic surfactants and emulsifiers.

The dyes according to the present disclosure may contain other auxiliaries and additives. Thus, it has proven advantageous when the agents contain at least one thickening agent. There are no restrictions in principle regarding these thickening agents. Both organic and purely inorganic thickening agents may be used.

Suitable thickening agents are
anionic, synthetic polymers;
cationic, synthetic polymers;
naturally occurring thickening agents, such as non-ionic guar gums, scleroglucan gums or xanthan gum, gum arabic, ghatti gum, karaya gum, tragacanth gum, carrageen gum, agar, carob seed meal, pectins, alginates, starch fractions and derivatives such as amylose, amylopectin, and dextrins, as well as cellulose derivatives, such as for example methyl cellulose, carboxymethyl celluloses, and hydroxyalkyl celluloses;
non-ionic, fully synthetic polymers, such as polyvinyl alcohol or polyvinylpyrrolidone; as well as
inorganic thickening agents, in particular phyllosilicates such as for example bentonite, particularly smectites, such as montmorillonite or hectorite.

The dyeing processes performed on the keratin fibers are usually run in an alkaline environment. To protect the keratin fibers as well as the skin as much as possible, however, it is not desirable to adjust to too high a pH value. Then, it is preferable when the pH value of the application-ready agent is between about 7 and about 11, in particular, between about 8 and about 10.5. The pH values within the meaning of the present disclosure are pH values that have been measured at a temperature of about 22° C.

The alkalizing agents that can be used according to the present disclosure to adjust the preferred pH value may be selected from the group consisting of ammonia, alkanolamines, basic amino acids, and inorganic alkalizing agents such as alkali/alkaline earth metal hydroxides, alkali/alkaline earth metal silicates, alkali/alkaline earth metal phosphates, and alkali/alkaline earth metal hydrogen phosphates. Preferred inorganic alkalizing agents are magnesium carbonate, sodium hydroxide, potassium hydroxide, sodium silicate, and sodium metasilicate. Organic alkalizing agents that can be used according to the present disclosure are preferably selected from monoethanolamine, 2-amino-2-methylpropanol, and triethanolamine. The basic amino acids that can be used as an alkalizing agent according to the present disclosure are preferably selected from the group consisting of arginine, lysine, ornithine, and histidine, especially preferably arginine. However, in the framework of the investigations conducted for the present disclosure, it has been found that agents that are preferred according to the present disclosure are furthermore wherein additionally containing an organic alkalizing agent. One embodiment of the first subject matter of the present disclosure is characterized in that the agent additionally contains at least one alkalizing agent selected from the group consisting of ammonia, alkanolamines, and basic amino acids, especially ammonia, monoethanolamine, and arginine or acceptable salts thereof.

It has furthermore proven advantageous when the dyes—especially when the dyes additionally contain hydrogen peroxide—contain at least one stabilizer or complexing agent. Especially preferred stabilizers are phenacetin, alkali bezonates (sodium benzoate), and salicylic acid. All complexing agents of the prior art may also be used. Complexing agents that are preferred according to the present disclosure are nitrogen-containing polycarboxylic acids, in particular, EDTA and EDDS as well as phosphonates, in particular, 1-hydroxyethane-1,1-diphosphonate (HEDP) and/or ethylenediamine tetramethylenephosphonate (EDTMP) and/or diethylenetriamine pentamethylenephosphonate (DTPMP) or sodium salts thereof.

The agents according to the present disclosure may moreover contain further active agents, auxiliaries, and additives, including for example non-ionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones, such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidinone copolymers quaternized with diethyl sulfate, vinylpyrrolidinone-imidazolinium-methochloride copolymers and quaternized polyvinyl alcohol; zwitterionic and amphoteric polymers; anionic polymers such as polyacrylic acids or crosslinked polyacrylic acids; structuring agents such as glucose, maleic acid and lactic acid, hair-conditioning compounds such as phospholipids, for example lecithin and cephalins; perfume oils, dimethyl isosorbide and cyclodextrins; active agents to improve the fiber structure, in particular mono-, di- and oligosaccharides such as for example glucose, galactose, fructose, fruit sugars and lactose; dyes for coloring the agent; anti-dandruff active agents such as piroctone olamine, zinc omadine, and climbazole; amino acids and oligopeptides; protein hydrolysates of animal and/or plant origin as well as those in the form of the fatty acid condensation products thereof or optionally anionically or cationically modified derivatives thereof; vegetable oils; light stabilizers and UV blockers; active agents such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols;

ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescing agents such as ethylene glycol mono- and distearate and PEG-3 distearate; pigments as well as propellants such as propane-butane mixtures, $N_2O$, dimethyl ether, $CO_2$, and air.

A person skilled in the art will arrive at the selection of these other substances according to the desired properties of the agents. For other optional components and the used quantities of these components, explicit reference is made to the relevant manuals that would be known to a person skilled in the art. The additional active ingredients and auxiliaries are preferably used in the agents according to the present disclosure in amounts of (respectively) about 0.0001 to about 25% by weight, in particular, about 0.0005 to about 15% by weight, relative to the total weight of the application mix.

With the dyes that contain the direct dyes of general formula (I) according to the present disclosure, keratinous fibers can be dyed in very attractive and intense shades of red. The dyes of general formula (I) are cationic dimeric azo dyes. Here, it has surprisingly been found that adding one or more anionic surfactants (b) of formula (B1) makes it possible to still further increase the color intensity of cationic azo dyes,

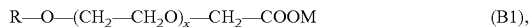

wherein
R represents a linear alkyl group having 8 to 30 C atoms,
x represents an integer from 0 to 16,
M represents hydrogen or a metal such as an alkali metal, in particular, sodium, potassium, or lithium,
an alkaline earth metal, in particular, ½ magnesium, ½ calcium, ½ zinc, or an ammonium ion ($NH_4^+$).

Another subject matter of the present disclosure is therefore the use of one or more anionic surfactants (b) of formula (B1)

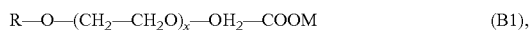

wherein
R represents a linear alkyl group having 8 to 30 C atoms,
x represents an integer from 0 to 16,
M represents hydrogen or a metal such as an alkali metal, in particular, sodium, potassium, or lithium, an alkaline-earth metal, in particular, ½ magnesium, ½ calcium, ½ zinc, or an ammonium ion ($NH_4^+$);
to improve the color take-up performance of direct dyes of general formula (I), as have been disclosed in the preceding description of the first subject matter of the present disclosure, onto keratinous fibers.

Improving the color take-up performance is understood in this context to mean that the dyes diffuse to an increased or intensified extent into the keratinous fibers, leading to coloration with a higher color intensity. The intensified color intensity can be detected either visually through observation under a daylight lamp or by colorimetric measurement (determining the Lab values).

It has surprisingly also been found that the color intensity of cationic azo dyes can also be increased by adding one or more cationic surfactants (b) of formula (B2),

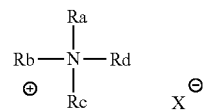

wherein
Ra, Rb represent—independently of one another—a $C_1$-$C_6$ alkyl group, a $C_2$-$C_6$ alkenyl group, or a $C_2$-$C_6$ hydroxyalkyl group;
Rc represents a $C_1$-$C_7$ alkyl group, a $C_8$-$C_{28}$ alkyl group, a $C_2$-$C_6$ alkenyl group, or a $C_2$-$C_6$ hydroxyalkyl group;
Rd represents a $C_8$-$C_{28}$ alkyl group, and
$X^-$ represents a physiologically acceptable anion.

Another subject matter of the present disclosure is therefore the use of one or more cationic surfactants (b) of formula (B2),

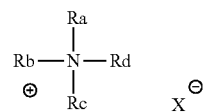

wherein
Ra, Rb represent—independently of one another—a $C_1$-$C_6$ alkyl group, a $C_2$-$C_6$ alkenyl group, or a $C_2$-$C_6$ hydroxyalkyl group;
Rc represents a $C_1$-$C_7$ alkyl group, a $C_8$-$C_{28}$ alkyl group, a $C_2$-$C_6$ alkenyl group, or a $C_2$-$C_6$ hydroxyalkyl group;
Rd represents a $C_8$-$C_{28}$ alkyl group, and
$X^-$ represents a physiologically acceptable anion.
to improve the color take-up performance of direct dyes, as have been disclosed in the preceding description of the first subject matter of the present disclosure, onto keratinous fibers.

The agents of the first subject matter of the present disclosure may be used in methods for dyeing and also in methods for simultaneously blonding or bleaching and dyeing human hair.

The agents according to the present disclosure may be formulated as a single-component agent or a multi-component agent, such as a two-component agent or three-component agent, and used accordingly. A separation into multi-component systems is particularly appropriate in cases where incompatibilities of the ingredients are to be expected or feared; in systems of this type, the ready-to-use agent is produced by the consumer by blending the components immediately prior to use. The agent for changing the color of keratinous fibers according to the present disclosure is always understood to mean the application-ready agent.

If the agent according to the present disclosure is made available to the user in the form of a single-component agent, then the usage-ready agent need not be prepared first, but instead can be removed directly from the container in which it has been produced and applied to the keratinous fibers.

Blonding agents, however, usually entail two-component products with which an oxidizing agent-containing component (A1) is mixed with an (alkalizing) agent (A2) shortly before use, and this application-ready mixture is applied to the hair.

In this case, the agent according to the present disclosure is the application-ready agent, which has been prepared shortly before use through mixing of (A1) and (A2).

Here, the direct dyes of general formula (I) may be prepared in the component (A1) (i.e., together with the oxidizing agent) or in the component (A2) (together with the alkalizing agent). The anionic and/or cationic surfactant (b) may here be contained in the component (A1) and/or in the component (A2).

It is also possible and in accordance with the present disclosure when the application-ready agent is prepared shortly before use on the human hair through mixing of three components, wherein the component (A1) contains at least one direct dye of general formula (I) and at least one alkalizing agent, the component (A2) contains at least one first oxidizing agent (e.g., hydrogen peroxide), and the component (A3) contains at least one second oxidizing agent (e.g., one or more peroxodisulfate salts). The anionic and/or cationic surfactant (b) may here be contained in the component (A1) and/or in the component (A2) and/or in the component (A3).

During the period of exposure of the fibers to the agent, it may be advantageous to assist the dyeing process by supplying heat. Heat may be supplied by an external heat source, such as for example hot air from a hot air blower, and also, in particular when lightening the hair of a living test subject, by the body temperature of the test subject. In the case of the latter possibility, the treated part is conventionally covered with a cap. Exposure at room temperature is likewise as contemplated herein. In particular, the temperature during the period of exposure is between 20° C. and 40° C., in particular, between 25° C. and 38° C. After the end of the period of exposure, the remaining coloring preparation is rinsed out of the hair with water or a cleaning agent. Conventional commercial shampoo may in particular be used here as the cleaning agent, wherein it is in particular possible to dispense with the cleaning agent and carry out the rinsing operation with water if the lightening agent has a carrier with a high surfactant content.

What has been stated regarding the agents according to the present disclosure also applies, mutatis mutandis, to other preferred embodiments of the use and method according to the present disclosure.

Examples

Direct dye 1: 5-[2-(4-{[3-({4[2-(1,4-Dimethyl-1H-1,2,4-triazol-4-ium-5-yl)diazen-1-yl]phenyl}-(methyl)amino)propyl](methyl)amino}phenyl)diazen-1-yl]-1,4-dimethyl-1H-1,2,4-triazol-4-ium di(methyl sulfate)

The dye DZ 1 was synthesized analogously to a method described in the documents WO 2002/100369 A2 and U.S. Pat. No. 3,291,788.

2-Amino-1,2,4-triazole and NN-dimethyl-N,N'-diphenyl-propan-1,3-diamine were used as reactants (azo coupling reaction in an aqueous, sulfuric solution with nitrosylsulfuric acid). The neutral dyes resulting from this azo coupling reaction were subsequently quaternized (for example, with the quaternizing agent dimethyl sulfate in a polar, aprotic solvent such as dimethyl formamide or dimethyl sulfoxide).

DZ 1 (According to the Present Disclosure)

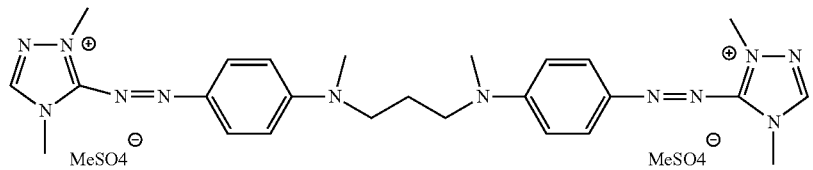 [SMILES: CN(CCCN(C)c1ccc(N=Nc2n(C)cn[n+]2C)cc1)c1ccc(N=Nc2n(C)cn[n+]2C)cc1]

Dye Examples

Formulations
The following dye creams were produced (all amounts in % by weight, active ingredient)

|  | V1 | E1 | E2 |
|---|---|---|---|
| Cetearyl Alcohol ($C_{16}/C_{18}$ fatty alcohol) | 1.0 | 1.0 | 1.0 |
| Coconut Alcohol ($C_{12}/C_{18}$ fatty alcohol) | 1.0 | 1.0 | 1.0 |
| Methylparaben | 0.1 | 0.1 | 0.1 |
| Propylparaben | 0.1 | 0.1 | 0.1 |
| Cocoamidopropyl betaine (zwitterionic surfactant) | 1.0 | — | — |
| Sodium laureth-5 carboxylate | — | 1.0 | — |
| Cetyl trimethyl ammonium chloride | — | — | 1.0 |
| DZ 1 (according to the present | 0.5 | 0.5 | 0.5 |
| Ammonium sulfate | 1.0 | 1.0 | 1.0 |
| Water | up to 100 | up to 100 | up to 100 |

The fatty alcohols (fat bodies) and the preservatives were each melted together with the surfactants. This melt was emulsified with hot water, then the dye that was pre-dissolved in the propylene glycol was added, as was the ammonium sulfate solution. The specified pH value was adjusted with ammonia, followed by filling to 100 g with water.

Colorations
Respectively, 1.8 g of the dye cream was applied to an approximately 6-cm-long strand of human hair (Kerling Euronaturhaar, 80% grayed) and left there for 30 minutes at 30° C. After the end of the exposure time, the hair was rinsed, washed with an ordinary hair washing agent, and then dried. After drying, the coloration and the color intensity of the strands were visually evaluated under a daylight lamp.

| Formulation |  | pH value | Color shade | Color intensity |
|---|---|---|---|---|
| V1 | DZ 1 and Cocoamidopropyl betaine | 9.5 | garnet red | +++ |
| E1 | DZ 1 and Sodium laureth-5 carboxylate | 9.5 | garnet red | +++++ |
| E2 | DZ 1 and Cetyl trimethyl ammonium | 9.5 | garnet red | +++++ |

Color intensity:
+ = poor
+++ = medium
+++++ = very good

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configurations of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinous fibers, the agent comprising, in a cosmetic carrier,
(a) at least one direct dye of formula (I),

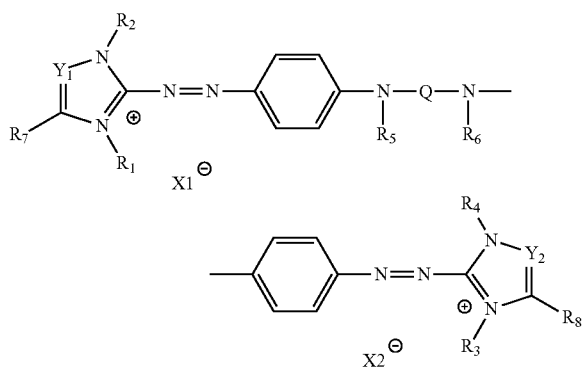

wherein
R1, R2, R3, R4 represent, independently of one another, a $C_1$-$C_6$ alkyl group, a $C_2$-$C_6$ alkenyl group, or a hydroxy $C_2$-$C_6$ alkyl group;
R5, R6 represent, independently of one another, a hydrogen atom, a $C_1$-$C_6$ alkyl group, a $C_2$-$C_6$ alkenyl group, a hydroxy $C_2$-$C_6$ alkyl group, or a cyano $C_1$-$C_6$ alkyl group;
R7, R8 represent, independently of one another, a hydrogen atom, a $C_1$-$C_6$ alkyl group, a halogen atom from the group consisting of chlorine, bromine, fluorine, and/or iodine, or a $C_1$-$C_6$ alkoxy group; wherein at least one of R5, R6, R7, and R8 does not represent a hydrogen atom;
X1, X2 represent, independently of one another, a physiologically acceptable anion, chloride, bromide, iodide, methyl sulfate, methyl sulfonate, p-toluenesulfonate, acetate, hydrogen sulfate, ½ sulfate, or ½ tetrachlorozincate;
Q represents a group of formula (II);

n represents an integer from 3 to 6; and
(b) at least one anionic surfactant and/or at least one cationic surfactant.

2. The agent according to claim 1, wherein the agent comprises (a) at least one direct dye of general formula (I), in which
R1, R2, R3, R4 represent, independently of one another, a methyl group or an ethyl group, and
R5, R6 represent, independently of one another, a hydrogen atom, a methyl group, or an ethyl group.

3. The agent according to claim 1, wherein the agent comprises (a) at least one direct dye of general formula (I), in which
R7, R8 each represent a hydrogen atom.

4. The agent according to claim 1, wherein the agent comprises (a) at least one direct dye of general formula (I) which is selected from:
salts of 5-[2-(4-{[3-({4[2-(1,4-dimethyl-1H-1,2,4-triazol-4-ium-5-yl)diazen-1-yl]phenyl}amino)propyl]amino}phenyl)diazen-1-yl]-1,4-dimethyl-1H-1,2,4-triazol-4-ium,
salts of 5-[2-(4-{[4-({4-[2-(1,4-Dimethyl-1H-1,2,4-triazol-4-ium-5-yl)diazen-1-yl]phenyl}amino)butyl)amino)phenyl)diazen-1-yl]-1,4-dimethyl-1H-1,2,4-triazol-4-ium,
salts of 5-[2-(4-{[5-({4-[2-(1,4-Dimethyl-1H-1,2,4-triazol-4-ium-5-yl)diazen-1-yl]phenyl}amino)pentyl]amino}phenyl)diazen-1-yl]-1,4-dimethyl-1H-1,2,4-triazol-4-ium,
salts of 5-[2-(4-{[3-({4[2-(1,4-Dimethyl-1H-1,2,4-triazol-4-ium-5-yl)diazen-1-yl]phenyl}-(methyl)amino)propyl](methyl)amino}phenyl)diazen-1-yl]-1,4-dimethyl-1H-1,2,4-triazol-4-ium,
salts of 5-[2-(4-{[4-({4-[2-(1,4-Dimethyl-1H-1,2,4-triazol-4-ium-5-yl)diazen-1-yl]phenyl}-(methyl)amino)butyl)(methyl)amino]phenyl}diazen-1-yl)-1,4-dimethyl-1H-1,2,4-triazol-4-ium,
salts of 5-[2-(4-{[5-({4[2-(1,4-Dimethyl-1H-1,2,4-triazol-4-ium-5-yl)diazen-1-yl]phenyl}-(methyl)amino)pentyl](methyl)amino}phenyl)diazen-1-yl]-1,4-dimethyl-1H-1,2,4-triazol-4-ium,
salts of 5-[2-(4-{[4-({4-[2-(1,4-Dimethyl-1H-1,2,4-triazol-4-ium-5-yl)diazen-1-yl]phenyl}-(ethyl)amino)propyl](ethyl)amino}phenyl)diazen-1-yl]-1,4-dimethyl-1H-1,2,4-triazol-4-ium,
salts of 5-[2-(4-{[4-({4-[2-(1,4-Dimethyl-1H-1,2,4-triazol-4-ium-5-yl)diazen-1-yl]phenyl}-(ethyl)amino)butyl](ethyl)amino}phenyl)diazen-1-yl]-1,4-dimethyl-1H-1,2,4-triazol-4-ium,
salts of 5-[2-(4-{[5-({4-[2-(1,4-Dimethyl-1H-1,2,4-triazol-4-ium-5-yl)diazen-1-yl]phenyl}-(ethyl)amino)pentyl](ethyl)amino}phenyl)diazen-1-yl]-1,4-dimethyl-1H-1,2,4-triazol-4-ium,
salts of 5-[2-(4-{[3-({442-(1,4-Diethyl-1H-1,2,4-triazol-4-ium-5-yl)diazen-1-yl}phenyl)-amino]propyl}amino}(phenyl)diazen-1-yl]-1,4-diethyl-1H-1,2,4-triazol-4-ium,
salts of 5-[2-(4-{[4-({4-[2-(1,4-Diethyl-1H-1,2,4-triazol-4-ium-5-yl)diazen-1-yl]phenyl]-amino)butyl]amino}phenyl)diazen-1-yl]-1,4-diethyl-1H-1,2,4-triazol-4-ium,
salts of 5-[2-(4-{[5-({4[2-(1,4-Diethyl-1H-1,2,4-triazol-4-ium-5-yl)diazen-1-yl]phenyl}amino)pentyl]amino}phenyl)diazen-1-yl]-1,4-diethyl-1H-1,2,4-triazol-4-ium,
salts of 5-[2-(4-{[3-({4[2-(1,4-Diethyl-1H-1,2,4-triazol-4-ium-5-yl)diazen-1-yl]phenyl}-(methyl)amino)propyl](methyl)amino}phenyl)diazen-1-yl]-1,4-diethyl-1H-1,2,4-triazol-4-ium,
salts of 5-[2-(4-{[4-({4-[2-(1,4-Diethyl-1H-1,2,4-triazol-4-ium-5-yl)diazen-1-yl]phenyl}-(methyl)amino)butyl)(methyl)amino]phenyl}diazen-1-yl)-1,4-diethyl-1H-1,2,4-triazol-4-ium,
salts of 5-[2-(4-{[5-({4-[2-(1,4-Diethyl-1H-1,2,4-triazol-4-ium-5-yl)diazen-1-yl]phenyl}-(methyl)amino)pentyl](methyl)amino}phenyl)diazen-1-yl)-1,4-diethyl-1H-1,2,4-triazol-4-ium, salts of 5-[2-(4-{[3-({4[2-(1,4-Diethyl-1H-1,2,4-triazol-4-ium-5-yl)diazen-1-yl]phenyl}-(ethyl)amino)propyl](ethyl)amino}phenyl)diazen-1-yl]-1,4-diethyl-1H-1,2,4-triazol-4-ium, salts of 5-[2-(4-{[4-({4-}2-(1,4-Diethyl-1H-1,2,4-triazol-4-ium-5-yl)diazen-1-yl]phenyl}-(ethyl)amino]butyl}(ethyl]amino]phenyl)diazen-1-yl]-1,4-diethyl-1H-1,2,4-triazol-4-ium, salts of 5-[2-(4-{[5-({4-[2-(1,4-Diethyl-1H-1,2,4-triazol-4-ium-5-yl)diazen-1-yl]phenyl}-(ethyl)amino)pentyl](ethyl)amino}phenyl)diazen-1-yl]-1,4-diethyl-1H-1,2,4-triazol-4-ium.

5. The agent according to claim 1, wherein the agent comprises, relative to the total weight of the agent, one or more direct dyes (a) of formula (I) in a total amount of about 0.01 to about 4.5% by weight.

6. The agent according to claim 1, wherein the agent comprises (b) at least one anionic surfactant selected from:
   linear and branched fatty acids having 8 to 30 C atoms;
   ether carboxylic acids of formula R—O—(CH$_2$—CH$_2$O)$_x$—CH$_2$—COOM, in which
   R represents a linear alkyl group having 8 to 30 C atoms,
   x represents an integer from 0 to 16,
   M represents hydrogen, a metal, an alkali metal, sodium, potassium, lithium, an alkaline-earth metal, ½ magnesium, ½ calcium, ½ zinc, or an ammonium ion (NH$_4^+$);
   acyl sarcosides having 8 to 24 C atoms in the acyl group; acyl taurides having 8 to 24 C atoms in the acyl group;
   acyl isethionates having 8 to 24 C atoms in the acyl group that can be obtained by esterification of C$_8$-C$_{24}$ fatty acids with the sodium salt of 2-hydroxyethane sulfonic acid (isethionic acid),
   amide ether carboxylic acids, R$^1$CO—NR$^2$—CH$_2$CH$_2$—O—(CH$_2$CH$_2$O)$_y$CH$_2$COOM, wherein
   R$^1$ represents a C$_2$-C$_{30}$ alkyl group,
   y represents an integer from 1 to 20,
   R$^2$ represents hydrogen or a methyl, ethyl, propyl, isopropyl, n-butyl, t-butyl, or isobutyl residue; and
   M represents hydrogen, a metal, an alkali metal, sodium, potassium, lithium, an alkaline-earth metal, ½ magnesium, ½ calcium, ½ zinc, or an ammonium ion (NH$_4^+$).

7. The agent according to claim 1, wherein the agent comprises, as the anionic surfactant, (b) at least one ether carboxylic acid of formula (B1),

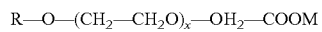  (B1), wherein
R represents a linear alkyl group having 8 to 30 C atoms,
x represents an integer from 5 to 11;
M represents hydrogen, a metal, an alkali metal, sodium, potassium, lithium, an alkaline-earth metal, ½ magnesium, ½ calcium, ½ zinc, or an ammonium ion (NH$_4^+$).

8. The agent according to claim 1, wherein the agent comprises, relative to the total weight of the agent, one or more anionic surfactants (b) in a total amount of about 0.05 to about 4.5% by weight.

9. The agent according to claim 1, wherein the agent comprises, as the cationic surfactant, (b) one or more compounds of formula (B2),

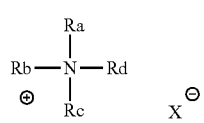  (B2)

wherein
Ra, Rb represent, independently of one another, a C$_1$-C$_6$ alkyl group, a C$_2$-C$_6$ alkenyl group, or a C$_2$-C$_6$ hydroxyalkyl group;
Rc represents a C$_1$-C$_7$ alkyl group, a C$_8$-C$_{28}$ alkyl group, a C$_2$-C$_6$ alkenyl group, or a C$_2$-C$_6$ hydroxyalkyl group;
Rd represents a C$_8$-C$_{28}$ alkyl group, and
X$^-$ represents a physiologically acceptable anion.

10. The agent according to claim 1, wherein the agent comprises one or more cationic surfactants (b) in a total amount of about 0.1 to about 4.8% by weight, relative to the total weight of the agent.

11. The agent according to claim 1, wherein the agent further comprises at least one other cationic direct dye that is different from the dyes of formula (I).

12. A method comprising using one or more anionic surfactants (b) of formula (B1)

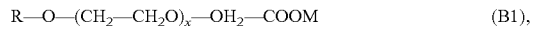  (B1), wherein
R represents a linear alkyl group having 8 to 30 C atoms,
x represents an integer from 5 to 11,
M represents hydrogen, a metal, an alkali metal, sodium, potassium, lithium, an alkaline-earth metal, ½ magnesium, ½ calcium, ½ zinc, or an ammonium ion (NH$_4^+$);
to improve the color take-up performance of direct dyes including at least one direct dye according to claim 1, into keratinous fibers.

13. A method comprising using one or more cationic surfactants (b) of formula (B2)

  (B2)

wherein
Ra, Rb both represent a methyl group or an ethyl group;
Rc represents a C$_1$-C$_7$ alkyl group, a C$_8$-C$_{28}$ alkyl group, a C$_2$-C$_6$ alkenyl group, or a C$_2$-C$_6$ hydroxyalkyl group;
Rd represents a C$_8$-C$_{28}$ alkyl group, and
X$^-$ represents a physiologically acceptable anion,
to improve the color take-up performance of direct dyes including at least one direct dye according to claim 1, into keratinous fibers.

14. The agent according to claim 1, wherein the agent comprises, relative to the total weight of the agent, one or more direct dyes (a) of formula (I) in a total amount of about 0.05 to about 2.8% by weight.

15. The agent according to claim 1, wherein the agent comprises, relative to the total weight of the agent, one or more direct dyes (a) of formula (I) in a total amount of about 0.1 to about 2.2% by weight.

16. The agent according to claim 1, wherein the agent comprises, relative to the total weight of the agent, one or more anionic surfactants (b) in a total amount of about 0.1 to about 3.1% by weight.

17. The agent according to claim 1, wherein the agent comprises, relative to the total weight of the agent, one or more anionic surfactants (b) in a total amount of about 0.15 to about 2.5% by weight.

18. The agent according to claim 1, wherein the agent comprises one or more cationic surfactants (b) in a total amount of about 0.2 to about 2.4% by weight, relative to the total weight of the agent.

19. The agent of claim 1 wherein R5 and R6 represent, independently of one another, a hydrogen atom, a methyl group or an ethyl group.

20. The method of claim 12 wherein x represents an integer from 5 to 7.

* * * * *